US012557864B2

(12) United States Patent
Toso

(10) Patent No.: US 12,557,864 B2
(45) Date of Patent: Feb. 24, 2026

(54) BACK SUPPORT DEVICE

(71) Applicant: Nada Concepts, Inc., St. Paul, MN (US)

(72) Inventor: Victor Toso, St. Paul, MN (US)

(73) Assignee: Nada Concepts, Inc., St. Paul, MN (US)

( * ) Notice: Subject to any disclaimer, the term of this patent is extended or adjusted under 35 U.S.C. 154(b) by 345 days.

(21) Appl. No.: 17/983,743

(22) Filed: Nov. 9, 2022

(65) Prior Publication Data

US 2023/0141821 A1 May 11, 2023

Related U.S. Application Data

(60) Provisional application No. 63/277,799, filed on Nov. 10, 2021.

(51) Int. Cl.
A61F 5/02 (2006.01)
A41D 13/05 (2006.01)
(Continued)

(52) U.S. Cl.
CPC ............ A41F 3/04 (2013.01); A41D 13/0531 (2013.01); A41D 13/1245 (2013.01); A61F 5/028 (2013.01)

(58) Field of Classification Search
CPC .. A61F 5/02; A61F 5/022; A61F 5/024; A61F 5/026; A61F 5/028; A61F 5/3776; A61F 5/03; A61H 1/0218; A61H 1/02; A61H 1/008; A61H 2201/1652; A47C 16/00; A47C 7/42; A41D 13/0531; A41D 13/1245; A45F 3/08; A61B 5/6831
See application file for complete search history.

(56) References Cited

U.S. PATENT DOCUMENTS 4,773,106 A 9/1988 Toso et al.
4,813,080 A 3/1989 Toso
(Continued)

FOREIGN PATENT DOCUMENTS

DE 202013008352 U1 10/2013
EP 0421045 A1 4/1991
(Continued)

OTHER PUBLICATIONS

Invitation to Pay Additional Fees dated Mar. 15, 2023 for International Application No. PCT/US2022/049392.

*Primary Examiner* — Ophelia A Hawthorne
(74) *Attorney, Agent, or Firm* — Seager, Tufte & Wickhem LLP

(57) ABSTRACT

A back support device for supporting a lower back of a user may include an elastic strap, a first clasping element attached to a first end of the elastic strap, a second clasping element slidably disposed over the elastic strap and configured to releasably engage the first clasping element to form a continuous loop, and a buckle element secured to a second end of the elastic strap. The buckle element is slidably disposed on a medial portion of the elastic strap for adjusting a perimeter length of the continuous loop. The continuous loop is movable between a first position in which the continuous loop has a first perimeter length and a second position in which the continuous loop has a second perimeter length via elastic elongation. The first perimeter length is less than the second perimeter length.

36 Claims, 34 Drawing Sheets

(51) Int. Cl.
   *A41D 13/12*          (2006.01)
   *A41F 3/04*           (2006.01)

(56)                     References Cited

U.S. PATENT DOCUMENTS

| | | | |
|---|---|---|---|
| 5,001,791 A | | 3/1991 | Toso |
| 5,083,554 A | | 1/1992 | Toso |
| 5,235,714 A | | 8/1993 | Toso |
| 5,236,714 A | | 8/1993 | Lee et al. |
| 5,375,279 A | | 12/1994 | Toso |
| 5,607,202 A | | 3/1997 | Toso et al. |
| 5,643,184 A | * | 7/1997 | Toso ........................ A61F 5/026 |
| | | | 450/155 |
| 5,645,080 A | | 7/1997 | Toso |
| 6,083,183 A | * | 7/2000 | Yang ........................ A61F 5/028 |
| | | | 2/311 |
| 6,086,157 A | | 7/2000 | Toso |
| 6,202,236 B1 | | 3/2001 | Price |
| 2006/0150293 A1 | | 7/2006 | Toso |
| 2006/0206992 A1 | | 9/2006 | Godshaw et al. |
| 2008/0195010 A1 | | 8/2008 | Lai et al. |
| 2009/0062705 A1 | | 3/2009 | Toso |
| 2016/0015547 A1 | | 1/2016 | Toso |

FOREIGN PATENT DOCUMENTS

| | | | | | |
|---|---|---|---|---|---|
| GB | 2582344 A | * | 9/2020 | ............. | A44B 11/04 |
| JP | S5828580 Y2 | | 6/1983 | | |
| JP | 2546657 Y2 | | 9/1997 | | |
| JP | H11107017 A | | 4/1999 | | |
| JP | 2005000506 A | | 1/2005 | | |
| JP | 3112564 U | | 8/2005 | | |
| JP | 2020130619 A | | 8/2020 | | |

* cited by examiner

BACK SUPPORT DEVICE

CROSS REFERENCE TO RELATED APPLICATIONS

This application claims the benefit of priority of U.S. Provisional Application No. 63/277,799 filed Nov. 10, 2021, the entire disclosure of which is hereby incorporated by reference.

TECHNICAL FIELD

The present disclosure relates generally to back support devices. More specifically, the present disclosure pertains to adjustable back support devices for supporting a lower back region of an individual in a seated position.

BACKGROUND

Many activities require participants to be seated in an upright position for an extended length of time without rigid back support. Examples of recreational activities which require an individual to be seated for extended periods of time include canoeing, fishing, hunting, boating, sports spectatorship, etc. Other activities such as working at a computer and/or traveling may also require an individual to be seated in an upright position for extended periods of time. In some cases, chairs and/or seating used and/or provided for such activities may be uncomfortable and/or offer inadequate back support, particularly for the lower back. Many people find sitting with little or no back support to be very uncomfortable or even painful, in some cases distracting from their participation in and/or enjoyment of these activities. Such discomfort may also cause the individual to reduce the amount of time they spend engaged in those activities. For example, during some activities, frequent stops and/or periods of standing may be required because of discomfort to the lower back. The frequency and severity of discomfort may be increased or exacerbated due to improper posture and/or a weak back structure.

A number of different back support devices have been developed which provide support to a user's lower back when seated. The ability to easily adjust these devices to provide a desired fit or to accommodate for variations in body size is often limited, however, preventing the user from comfortably wearing the device for extended periods of time. In some designs, for example, the back support device may not permit the user to adjust the size of the device in order to give the user a more relaxed fit and/or to improve body posture. In such case, the inability to adjust the device may limit its use. In some designs, the back support device may fall off of the user upon standing or may dangle in a way that interferes with comfortable standing or walking. A need therefore exists for back support devices that can be easily used and/or stored during use when a user needs to stand or walk.

SUMMARY

In one example, a back support device for supporting a lower back of a user may comprise an elastic strap, a first clasping element attached to a first end of the elastic strap, a second clasping element slidably disposed over the elastic strap and configured to releasably engage the first clasping element to form a continuous loop, and a buckle element secured to a second end of the elastic strap. The buckle element may be slidably disposed on a medial portion of the elastic strap for adjusting a perimeter length of the continuous loop. The continuous loop may be movable between a first position in which the continuous loop has a first perimeter length and a second position in which the continuous loop has a second perimeter length via elastic elongation. The first perimeter length may be less than the second perimeter length.

In addition or alternatively to any example described herein, in the first position the continuous loop may be secured around a torso of the user such that the continuous loop holds itself in place on the torso of the user and in the second position the continuous loop extends around the lower back of the user and at least one knee of the user in a seated position.

In addition or alternatively to any example described herein, in the second position the continuous loop may extend around the lower back of the user and two knees of the user.

In addition or alternatively to any example described herein, the first clasping element may include a non-elastic flap.

In addition or alternatively to any example described herein, the second clasping element may include a closed loop.

In addition or alternatively to any example described herein, the first clasping element may be configured to extend through the closed loop of the second clasping element and fold back on itself to form the continuous loop.

In addition or alternatively to any example described herein, the first clasping element may be configured to releasably secure to itself.

In addition or alternatively to any example described herein, the medial portion of the elastic strap may extend through the buckle element.

In addition or alternatively to any example described herein, a method of supporting a lower back of a user may comprise: positioning an elastic strap around a torso of the user, the elastic strap including a first end and a second end, the second end being secured to a buckle element slidably disposed on a medial portion of the elastic strap; releasably securing a first clasping element attached to the first end of the elastic strap to a second clasping element slidably disposed over the elastic strap to form a continuous loop around the torso of the user; sliding the buckle element along the medial portion of the elastic strap to secure the continuous loop around the torso of the user such that the continuous loop holds itself in place on the torso of the user in a first position, wherein the continuous loop has a first perimeter length in the first position; and moving the continuous loop from the first position to a second position in which the continuous loop extends around the lower back of the user and at least one knee of the user in a seated position, wherein the elastic strap elastically elongates from the first position to the second position such that in the second position the continuous loop has a second perimeter length greater than the first perimeter length.

In addition or alternatively to any example described herein, the buckle element may include a first end member, a second end member, a first side member extending from the first end member to the second end member, a second side member extending from the first end member to the second end member, and a central member disposed between the first side member and the second side member, the central member extending from the first end member to the second end member.

In addition or alternatively to any example described herein, the second end of the elastic strap may be fixedly secured to the central member and the medial portion of the elastic strap may extend between the first side member and the central member and the medial portion of the elastic strap may extend between the second side member and the central member.

In addition or alternatively to any example described herein, the method may comprise moving the continuous loop from the second position to the first position without any adjustment other than elastic contraction.

In addition or alternatively to any example described herein, the continuous loop may radially constrict upon the torso of the user in the first position.

In addition or alternatively to any example described herein, the method may comprise sliding the buckle element along the medial portion of the elastic strap in the first position to change a radially inward force exerted by the continuous loop against the lower back of the user in the second position.

In addition or alternatively to any example described herein, a back support device for supporting a lower back of a user may comprise an elongate piece of elastic material, a first clasping element attached to a first end of the elongate piece of elastic material, a buckle element secured to a second end of the elongate piece of elastic material, and a second clasping element slidably disposed over the elongate piece of elastic material and configured to releasably engage the first clasping element. A medial portion of the elongate piece of elastic material may pass through the buckle element such that the buckle element is disposed at a buckle position along the medial portion. The second clasping element may be slidably disposed over the elongate piece of elastic material between the second end of the elongate piece of elastic material and the buckle position. The back support device may be movable, without changing the buckle position, between a first position in which the back support device forms a continuous loop extending around and elastically constricting upon a torso of the user and a second position in which the continuous loop extends around the lower back of the user and at least one knee of the user in a seated position.

In addition or alternatively to any example described herein, the continuous loop may have a first perimeter length in the first position and a second perimeter length in the second position, the second perimeter length being greater than the first perimeter length.

In addition or alternatively to any example described herein, the back support device may be movable between the first position and the second position only via elasticity of the elongate piece of elastic material.

In addition or alternatively to any example described herein, the first clasping element may include an aperture extending therethrough and a projecting element fixedly attached thereto, wherein the projecting element may be configured to extend through the aperture to secure the first clasping element to itself when the first clasping element is engaged with the second clasping element to form the continuous loop.

In addition or alternatively to any example described herein, the first clasping element may comprise leather and the projecting element may be a metal stud.

In addition or alternatively to any example described herein, the elongate piece of elastic material may include a first layer and a second layer, wherein at least a portion of the first clasping element may extend between the first layer and the second layer of the elongate piece of elastic material.

In addition or alternatively to any example described herein, a back support device for supporting a lower back of a user may comprise an elastic strap, a first clasping element attached to a first end of the elastic strap, a first buckle element secured to a second end of the elastic strap and slidably disposed over a medial portion of the elastic strap, a second buckle element slidably disposed over the elastic strap and configured to releasably engage the first clasping element to form a continuous loop, and a third buckle element slidably disposed over the elastic strap between the first buckle element and the second buckle element. A plurality of segments of the elastic strap may be defined by the first buckle element, the second buckle element, and the third buckle element, and the plurality of segments circumferentially overlap between the first buckle element and the second buckle element.

In addition or alternatively to any example described herein, the plurality of segments includes a first segment extending between the first buckle element and the second buckle element, a second segment extending between the second buckle element and the third buckle element, a third segment extending between the third buckle element and the second buckle element, a fourth segment extending between the second buckle element and the third buckle element, and a fifth segment extending between the third buckle element and the first buckle element.

In addition or alternatively to any example described herein, the first segment is disposed radially outward of all other segments of the plurality of segments.

In addition or alternatively to any example described herein, the second segment is disposed radially inward of the first segment, the third segment is disposed radially inward of the second segment, and the fourth segment is disposed radially inward of the third segment.

In addition or alternatively to any example described herein, the continuous loop is to movable between a first position in which the continuous loop is secured around a torso of the user such that the continuous loop holds itself in place on the torso of the user and a second position in which the continuous loop extends around the lower back of the user and at least one knee of the user.

In addition or alternatively to any example described herein, the continuous loop is movable between the first position and the second position via a combination of movement of the third buckle element and elastic elongation of the elastic strap.

In addition or alternatively to any example described herein, the continuous loop exerts a radially inward force against the lower back of the user in the second position to support the lower back of the user.

In addition or alternatively to any example described herein, in the second position, the first buckle element is disposed at a first buckle position, and the continuous loop is movable between the first position and the second position without moving the first buckle element from the first buckle position.

In addition or alternatively to any example described herein, a method of supporting a lower back of a user may comprise: positioning an elastic strap around a torso of the user, the elastic strap including a first end and a second end, the second end being secured to a first buckle element slidably disposed on a medial portion of the elastic strap; releasably securing a first clasping element attached to the first end of the elastic strap to a second buckle element slidably disposed over the elastic strap to form a continuous loop around the torso of the user in a first position; moving the continuous loop from the first position to a second position in which the continuous loop extends around the lower back of the user and at least one knee of the user in a seated position such that the continuous loop exerts a radially inward force against the lower back of the user; sliding the first buckle element along the medial portion of the elastic strap to change the radially inward force applied to the lower back of the user in the second position, the first buckle element being disposed in a first buckle position when the radially inward force is at a desired level; and moving the continuous loop from the second position to the first position without moving the first buckle element from the first buckle position, wherein the elastic strap elastically contracts such that a perimeter length of the continuous loop in the first position that is less than the perimeter length of the continuous loop in the second position.

In addition or alternatively to any example described herein, moving the continuous loop from the second position to the first position includes sliding a third buckle element over the medial portion of the elastic strap to secure the continuous loop around the torso of the user such that the continuous loop holds itself in place on the torso of the user in the first position.

In addition or alternatively to any example described herein, the third buckle element is disposed between the first buckle element and the second buckle element.

In addition or alternatively to any example described herein, moving the continuous loop from the second position to the first position includes sliding the third buckle element over the medial portion of the elastic strap towards the first buckle element.

In addition or alternatively to any example described herein, sliding the third buckle element over the medial portion of the elastic strap towards the first buckle element forms a plurality of segments of the elastic strap defined by the first buckle element, the second buckle element, and the third buckle element. The plurality of segments may circumferentially overlap between the first buckle element and the second buckle element.

In addition or alternatively to any example described herein, sliding the third buckle element over the medial portion of the elastic strap takes up slack in the elastic strap disposed between the first buckle element and the second buckle element when the continuous loop is disposed in the first position.

In addition or alternatively to any example described herein, sliding the third buckle element over the medial portion of the elastic strap draws the second buckle element closer to the first buckle element.

In addition or alternatively to any example described herein, moving the continuous loop from the first position to the second position elastically elongates the elastic strap.

In addition or alternatively to any example described herein, a kiosk for marketing a back support device for supporting a lower back of a user may comprise a seat including a seating surface and a backrest, a back support device secured to the backrest, and a vending machine configured to hold stock of the back support device therein. The back support device may comprise an elastic strap, a first clasping element attached to a first end of the elastic strap, a first buckle element secured to a second end of the elastic strap and slidably disposed over a medial portion of the elastic strap, and a second buckle element slidably disposed over the elastic strap and configured to releasably engage the first clasping element to form a continuous loop. The continuous loop may be movable between a first position in which the continuous loop is secured around a torso of the user and a second position in which the continuous loop extends around the lower back of the user and at least one knee of the user in a seated position via elastic elongation.

In addition or alternatively to any example described herein, the seat further includes a safety belt secured thereto.

In addition or alternatively to any example described herein, the stock includes individually packaged back support devices.

In addition or alternatively to any example described herein, the back support device is secured to the backrest in a theft resistant manner.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which.

Figure 1:
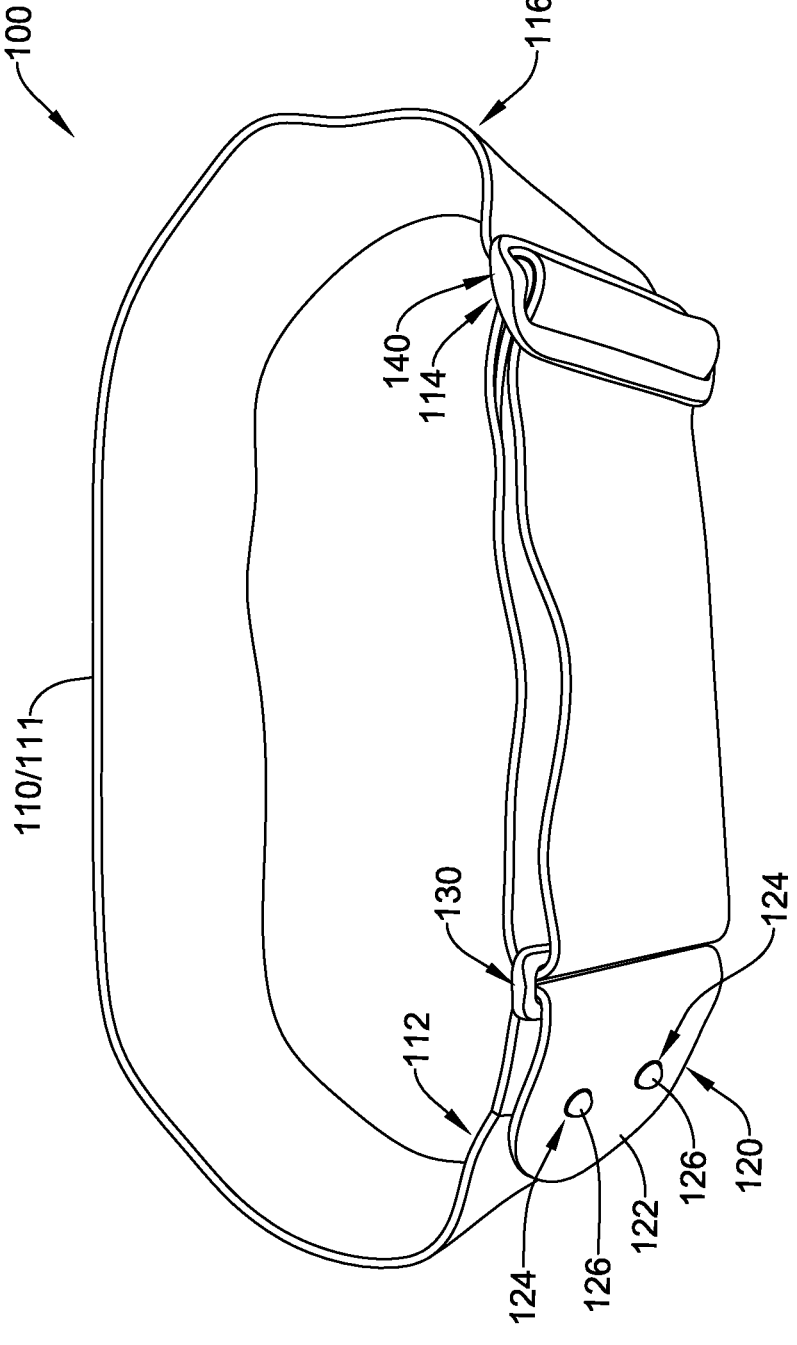
FIGS. 1-6 illustrate selected aspects of a back support device according to the disclosure.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal" and "distal", variants thereof, and the like, may be generally considered with respect to the positioning, direction, and/or operation of various elements relative to a user/operator/manipulator or a reference point of the device, wherein "proximal" indicates or refers to closer to or toward the user or reference point and "distal" indicates or refers to farther from or away from the user or reference point. In some instances, the terms "proximal" and "distal" may be arbitrarily assigned in an effort to facilitate understanding of the disclosure, and such instances will be readily apparent to the skilled artisan. Other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some features and/or reference numbers may not be shown in each figure for clarity. Similarly, each and every element and/or reference number may not be discussed in detail with respect to each figure. Some reference numbers and/or features may be shown and/or described in other figures in more detail, and those reference numbers and/or features may be shown and/or identified in some figures merely for reference.

FIG. 1 illustrates selected aspects of one example of a back support device 100 for supporting a lower back of a user in a seated position, according to the disclosure. The back support device 100 may include an elastic strap 110 and/or an elongate piece of elastic material 111. In some embodiments, the elongate piece of elastic material 111 may be formed into the elastic strap 110. The elastic strap 110 and/or the elongate piece of elastic material 111 may include and/or may have a first end 112 and a second end 114 opposite the first end 112. In some embodiments, the elastic strap 110 and/or the elongate piece of elastic material 111 may be continuously and/or entirely elastic from the first end 112 to the second end 114. In some alternative embodiments, the elastic strap 110 and/or the elongate piece of elastic material 111 may include a plurality of segments, wherein one or more segments of the plurality of segments of the elastic strap 110 and/or the elongate piece of elastic material 111 may include a non-elastic material. In some embodiments, the elastic strap 110 and/or the elongate piece of elastic material 111 may be discontinuously elastic from the first end 112 to the second end 114. In one example, the elastic strap 110 and/or the elongate piece of elastic material 111 may include a non-elastic segment at and/or adjacent the first end 112 and/or the second end 114. In another example, elastic material and non-elastic material may alternate along the length of the elastic strap 110 and/or the elongate piece of elastic material 111 from the first end 112 to the second end 114. Other configurations are also contemplated.

In some embodiments, the elastic strap 110 and/or the elongate piece of elastic material 111 may include a plurality of layers. In some embodiments, the elastic strap 110 and/or the elongate piece of elastic material 111 may be formed and/or folded over on itself to form a first layer 111A and a second layer 111B (e.g., FIG. 3A). In some embodiments, the plurality of layers and/or the first layer 111A and the second layer 111B may extend from the first end 112 of the elastic strap 110 and/or the elongate piece of elastic material 111 to the second end 114 of the elastic strap 110 and/or the elongate piece of elastic material 111. In some embodiments, the plurality of layers and/or the first layer 111A and the second layer 111B may be fixedly attached together, such as with adhesive bonding, stitching, other fastening means, etc. In some embodiments, the elastic strap 110 and/or the elongate piece of elastic material 111 may be a single monolithic piece of material. In some embodiments, the plurality of layers and/or the first layer 111A and the second layer 111B may be formed from a single monolithic piece of material. Other configurations are also contemplated.

In some embodiments, the back support device 100 may include a first clasping element 120 secured and/or attached to the first end 112 of the elastic strap 110 and/or the elongate piece of elastic material 111. In some embodiments, the first clasping element 120 may be fixedly secured and/or fixedly attached to the first end 112 of the elastic strap 110 and/or the elongate piece of elastic material 111. In some embodiments, the first clasping element 120 may be non-removable from the elastic strap 110 and/or the elongate piece of elastic material 111. Other configurations are also contemplated.

In some embodiments, the back support device 100 may include a second clasping element 130 slidably disposed over and/or on the elastic strap 110 and/or the elongate piece of elastic material 111. In some embodiments, the second clasping element 130 may include a closed loop (e.g., FIG. 2). In some embodiments, a medial portion 116 of the elastic strap 110 and/or the elongate piece of elastic material 111 may pass through the second clasping element 130. In some embodiments, the second clasping element 130 may be configured to slide over and/or along the medial portion 116 of the elastic strap 110 and/or the elongate piece of elastic material 111. In some embodiments, the second clasping element 130 may be non-removable from the elastic strap 110 and/or the elongate piece of elastic material 111. Other configurations are also contemplated.

In some embodiments, the second clasping element 130 may be configured to releasably engage the first clasping element 120 to form the back support device 100 into a continuous loop. In some embodiments, the first clasping element 120 and the second clasping element 130 may collectively form and/or comprise a clasping mechanism configured to form the back support device 100 into the continuous loop. In some embodiments, the first clasping element 120 and the second clasping element 130, and/or the clasping mechanism, may form the back support device 100 into a belt or a belt-like structure configured to be secured around the torso of a user. In at least some embodiments, the back support device 100 may define and/or include only a single continuous loop or only one continuous loop. Other configurations are also contemplated.

In some embodiments, the back support device 100 may include a buckle element 140 secured to the second end 114 of the elastic strap 110 and/or the elongate piece of elastic material 111. In some embodiments, the buckle element 140 may be slidably disposed on the medial portion 116 of the elastic strap 110 and/or the elongate piece of elastic material 111 for adjusting a perimeter length of the continuous loop. In some embodiments, the medial portion 116 of the elastic strap 110 and/or the elongate piece of elastic material 111 may extend and/or pass through the buckle element 140. In some embodiments, the buckle element 140 may be configured to selectively slide over and/or along the medial portion 116 of the elastic strap 110 and/or the elongate piece of elastic material 111. In some embodiments, the buckle element 140 may be non-removable from the elastic strap 110 and/or the elongate piece of elastic material 111. Other configurations are also contemplated.

Figure 2:
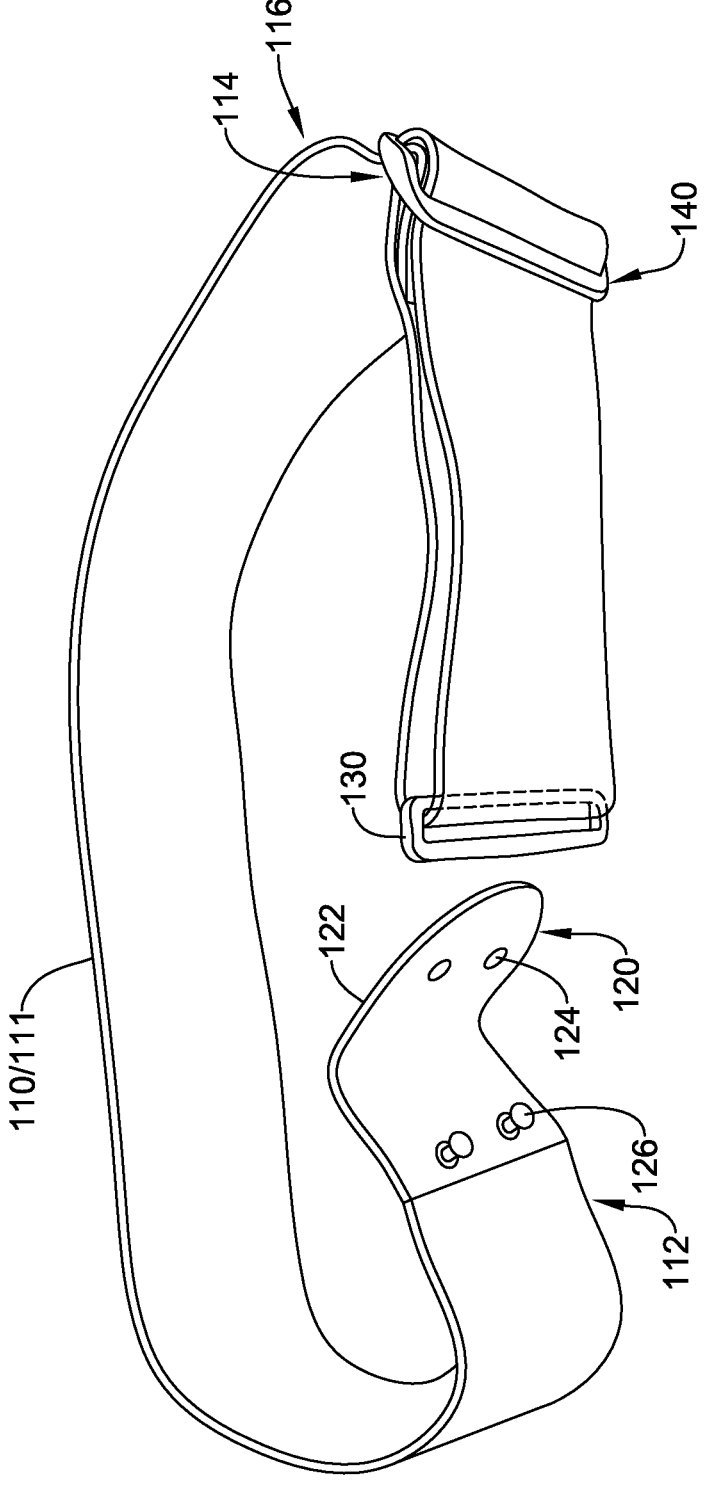

In some embodiments, the first clasping element 120 may include a non-elastic flap 122, as seen in FIG. 2. In some embodiments, the first clasping element 120 may include an aperture 124 extending therethrough. In some embodiments, the first clasping element 120 may include a plurality of apertures (e.g., a first aperture, a second aperture, etc.). In some embodiments, the first clasping element 120 may include a projecting element 126 fixedly attached thereto. In some embodiments, the projecting element 126 may extend through the first clasping element 120 and/or the non-elastic flap 122. In some embodiments, the first clasping element 120 may include a plurality of projecting elements (e.g., a first projecting element, a second projecting element, etc.). In some embodiments, the first clasping element 120 and/or the non-elastic flap 122 may comprise leather or another non-elastic material. Other configurations are also contemplated. In some embodiments, the projecting element 126 may include and/or may be a metal stud. In some embodiments, the projecting element 126 and/or the metal stud may include an enlarged tip at its free end. Other configurations are also contemplated.

Figure 3:
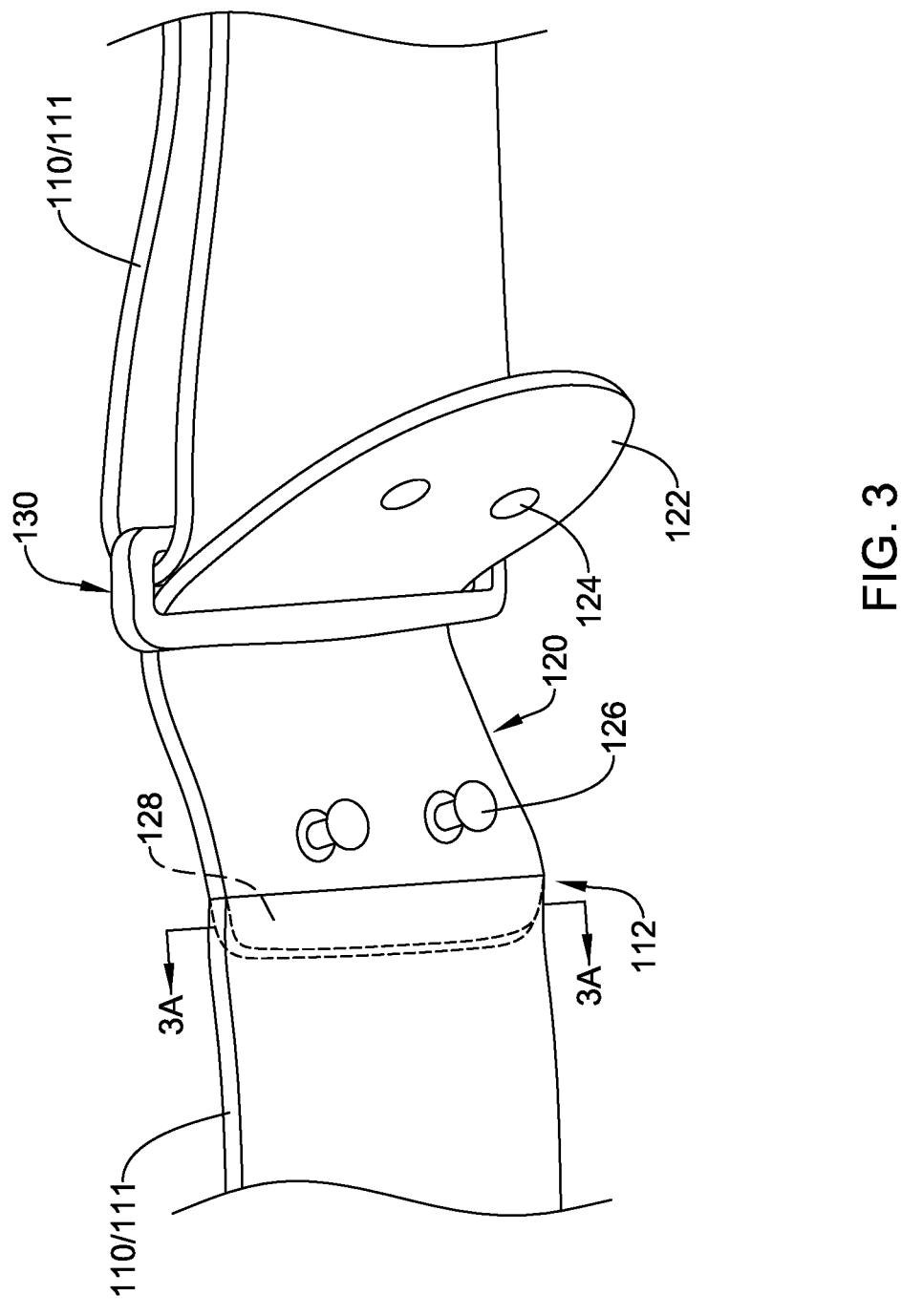
Figure 3A:
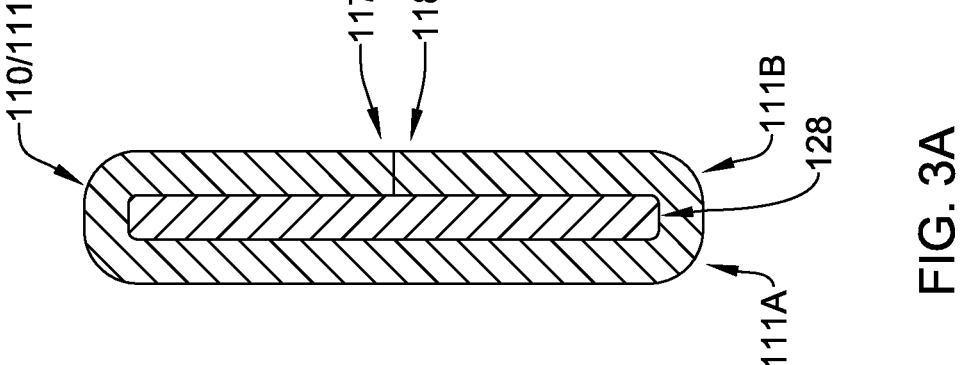

As seen in FIG. 3, the first clasping element 120 and/or the non-elastic flap 122 may be configured to releasably engage the second clasping element 130. In some embodiments, at least a portion 128 of the first clasping element 120 and/or the non-elastic flap 122 is fixedly secured and/or fixedly attached to the first end 112 of the elastic strap 110 and/or the elongate piece of elastic material 111. In at least some embodiments, the at least a portion 128 of the first clasping element 120 and/or the non-elastic flap 122 extends between the first layer 111A and the second layer 111B of the elastic strap 110 and/or the elongate piece of elastic material 111, as seen in FIG. 3A. The at least a portion 128 of the first clasping element 120 and/or the non-elastic flap 122 may be fixedly secured and/or fixedly attached to the first layer 111A and the second layer 111B of the elastic strap 110 and/or the elongate piece of elastic material 111.

In some embodiments, the elastic strap 110 and/or the elongate piece of elastic material 111 may include a top edge 117 and a bottom edge 118 that may be brought and/or held together adjacent and/or abutting each other when the elastic strap 110 and/or the elongate piece of elastic material 111 is formed and/or folded over into the first layer 111A and the second layer 111B. In some embodiments, the top edge 117 and the bottom edge 118 of the elastic strap 110 and/or the elongate piece of elastic material 111 may be stitched and/or fixedly attached together and/or to each other along an entire length of the elastic strap 110 and/or the elongate piece of elastic material 111. Other configurations are also contemplated.

Figure 4:
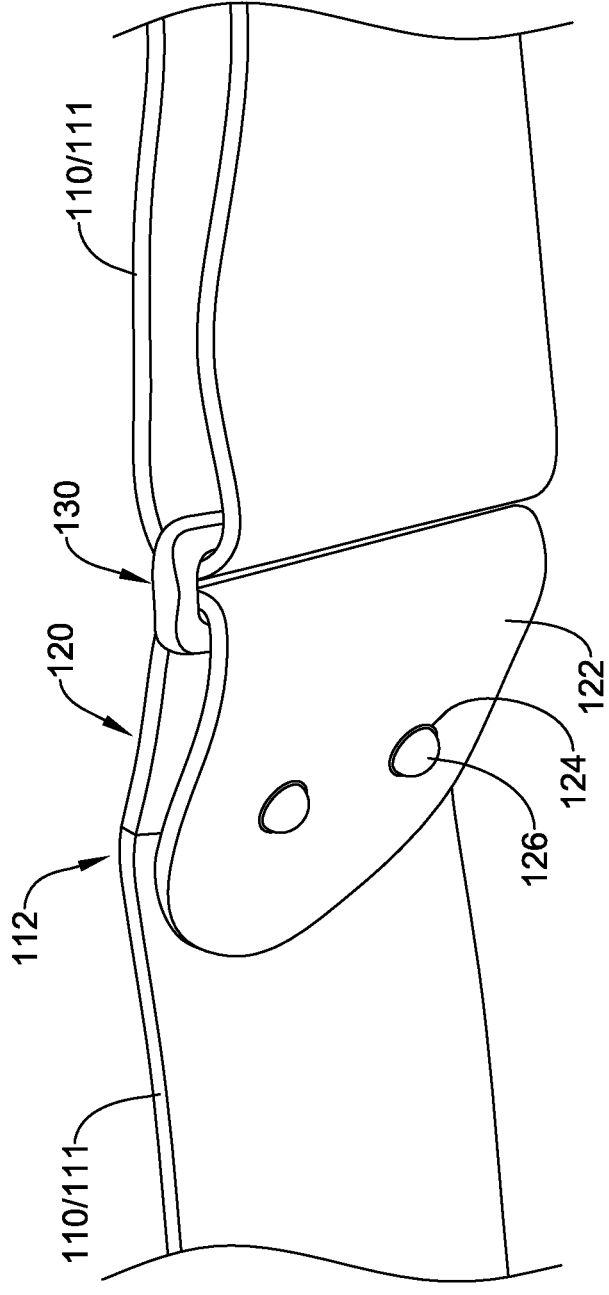

In some embodiments, the first clasping element 120 and/or the non-elastic flap 122 may be configured to extend through the closed loop of the second clasping element 130 as seen in FIG. 3 and fold back on itself to form the continuous loop, as seen in FIG. 4. The projecting element 126 may be configured to engage and/or extend through the aperture 124 to secure the first clasping element 120 to itself when the first clasping element 120 and/or the non-elastic flap 122 is engaged with the second clasping element 130 to form the continuous loop. In some embodiments, the plurality of projecting elements may be configured to engaged with and/or extend through the plurality of apertures to secure the first clasping element 120 to itself when the first clasping element 120 and/or the non-elastic flap 122 is engaged with the second clasping element 130 to form the continuous loop. Other configurations are also contemplated.

Figure 5:
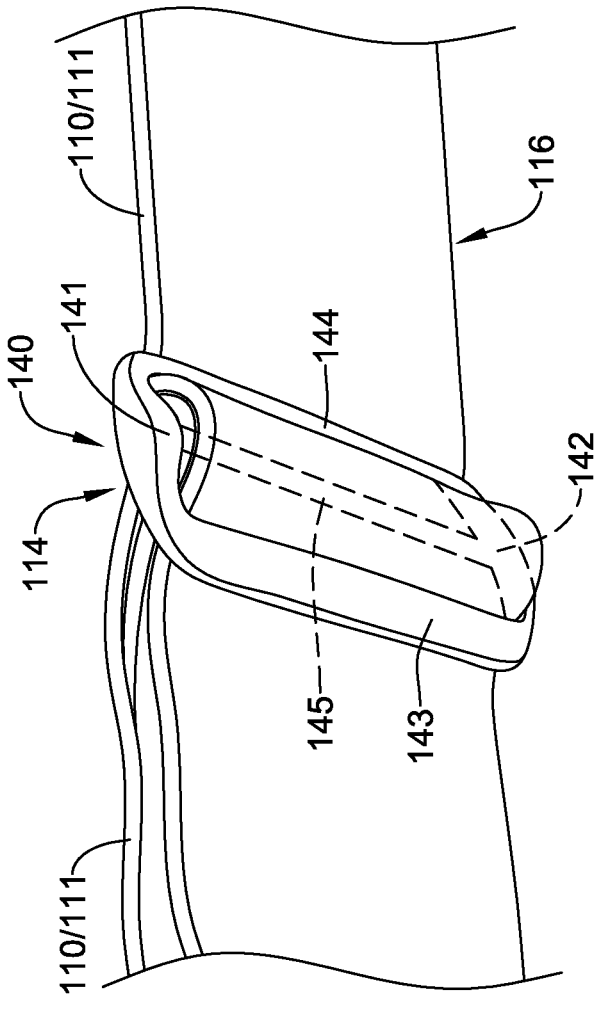

Turning to FIG. 5, the buckle element 140 may be secured to the second end 114 of the elastic strap 110 and/or the elongate piece of elastic material 111. In some embodiments, the buckle element 140 may include a first end member 141 and a second end member 142 opposite the first end member 141. In some embodiments, the buckle element 140 may include a first side member 143 extending from the first end member 141 to the second end member 142. In some embodiments, the buckle element 140 may include a second side member 144 extending from the first end member 141 to the second end member 142. In some embodiments, the buckle element 140 may include a central member 145 extending from the first end member 141 to the second end member 142. In some embodiments, the second side member 144 may be disposed opposite the first side member 143 relative to the central member 145.

Figure 6:
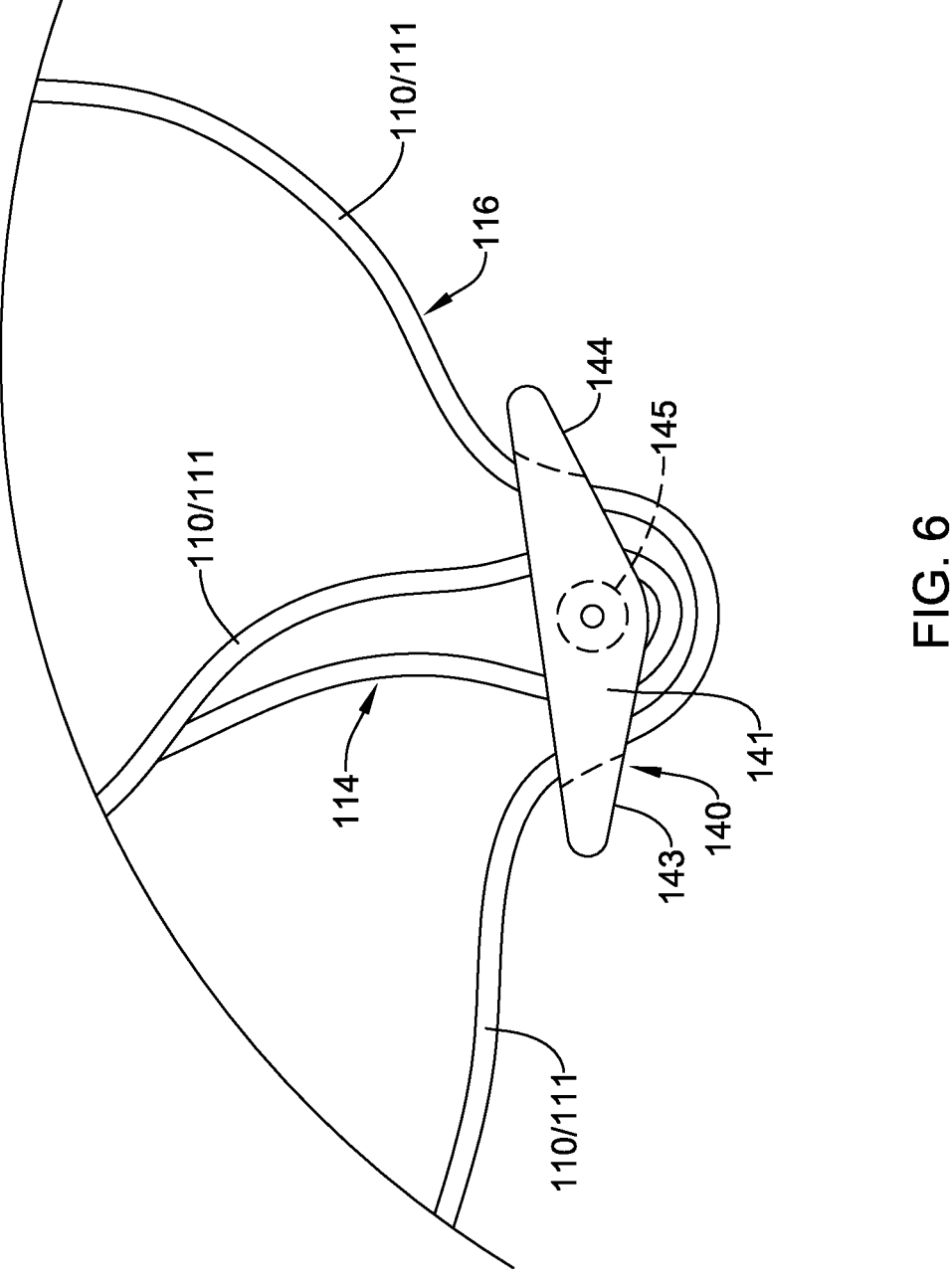

In some embodiments, the second end 114 of the elastic strap 110 and/or the elongate piece of elastic material 111 may be secured to the central member 145 of the buckle element 140. In some embodiments, the second end 114 of the elastic strap 110 and/or the elongate piece of elastic material 111 may be fixedly secured to the central member 145 of the buckle element 140 such that the second end 114 of the elastic strap 110 and/or the elongate piece of elastic material 111 is non-removable and/or non-detachable from the buckle element 140 and/or the central member 145 of the buckle element 140. In some embodiments, the medial portion 116 of the elastic strap 110 and/or the elongate piece of elastic material 111 may extend and/or may pass between the first side member 143 and the central member 145 of the buckle element 140, as seen in FIGS. 5 and 6. In some embodiments, the medial portion 116 of the elastic strap 110 and/or the elongate piece of elastic material 111 may extend and/or may pass between the second side member 144 and the central member 145 of the buckle element 140.

As it relates to the continuous loop shown in FIG. 1, the medial portion 116 of the elastic strap 110 and/or the elongate piece of elastic material 111 may pass inside of the first side member 143 and/or an inwardly facing surface of the first side member 143, between the first side member 143 and the central member 145, outside of and/or around an outwardly facing surface of the central member 145, between the second side member 144 and the central member 145, and inside of the second side member 144 and/or an inwardly facing surface of the second side member 144, as shown in FIG. 6. In some embodiments, tension applied to the medial portion 116 of the elastic strap 110 and/or the elongate piece of elastic material 111 and/or to the continuous loop may urge the medial portion 116 of the elastic strap 110 and/or the elongate piece of elastic material 111 against the central member 145 of the buckle element 140 such that at least a portion of the elastic strap 110 and/or the elongate piece of elastic material 111 is pinched against the central member 145. The buckle element 140 may be disposed at a buckle position (e.g., marked on the elastic strap 110 and/or the elongate piece of elastic material 111 in FIGS. 9, 11-13 with an "X") along the medial portion 116 of the elastic strap 110 and/or the elongate piece of elastic material 111. Friction between the pinched portion of the elastic strap 110 and/or the elongate piece of elastic material 111 and the medial portion 116 of the elastic strap 110 and/or the elongate piece of elastic material 111 being pulled and/or urged against the pinched portion of the elastic strap 110 and/or the elongate piece of elastic material 111 may effectively lock the buckle element 140 in place at the buckle position along the medial portion 116 of the elastic strap 110 and/or the elongate piece of elastic material 111.

In at least some embodiments, the second clasping element 130 may be slidably disposed over and/or on along the medial portion 116 of the elastic strap 110 and/or the elongate piece of elastic material 111 between the second end 114 of the elastic strap 110 and/or the elongate piece of elastic material 111 and the buckle element 140, as seen in FIG. 1. In some embodiments, the second clasping element 130 may be slidably disposed over and/or on along the medial portion 116 of the elastic strap 110 and/or the elongate piece of elastic material 111 between the second end 114 of the elastic strap 110 and/or the elongate piece of elastic material 111 and the buckle position.

In some embodiments, having the elastic strap 110 and/or the elongate piece of elastic material 111 "doubled up" through the buckle element 140, as shown in FIGS. 5-6, may create and/or result in difficulty moving the buckle element 140 along the medial portion 116 of the elastic strap 110 and/or the elongate piece of elastic material 111 for adjustment purposes. In some alternative embodiments, the second end 114 of the elastic strap 110 and/or the elongate piece of elastic material 111 may include a thinned fastening element fixedly attached thereto, wherein the thinned fastening element passes through the buckle element 140 and/or around the central member 145 of the buckle element 140, thereby reducing bulk between the first side member 143 and the central member 145 and between the second side member 144 and the central member 145 to permit easier adjustment of the buckle position. The thinned fastening element may include and/or have a thickness that is less than a thickness of the elastic strap 110 and/or the elongate piece of elastic material 111. In some embodiments, the thinned fastening element may be and/or include an elastic material. In some embodiments, the thinned fastening element may be and/or include the same elastic material as the elastic strap 110 and/or the elongate piece of elastic material 111. Alternatively, in some embodiments, the thinned fastening element may be and/or include a non-elastic material. Other configurations are also contemplated.

In some embodiments, the second clasping element 130 may be a second buckle element. In some embodiments, there may be no additional structure, no additional buckle element(s), and/or no additional clasping element(s) between the buckle element 140 and the second buckle element. In some embodiments, the second buckle element may be substantially the same as the buckle element 140 and/or the second buckle element may be a second instance of the buckle element 140 (e.g., the back support device 100 may have two of the buckle element 140). For descriptive purposes only, individual features, elements, and/or components of the second buckle element will be referred to using the same reference numbers applied to the buckle element 140 seen in FIG. 5 for example. The use of these reference numbers is not intended to be limiting and is merely meant to enhance understanding with respect to the second buckle element described herein.

In some embodiments having the second buckle element, such as those having no additional structure, no additional buckle element(s), and/or no additional clasping element(s) between the buckle element 140 and the second buckle element, a path of the elastic strap 110 and/or the elongate piece of elastic material 111 may extend inside of the second side member 144 and/or an inwardly facing surface of the second side member 144, between the second side member 144 and the central member 145, outside of and/or around an outwardly facing surface of the central member 145, between the first side member 143 and the central member 145, outside of and/or around an outwardly facing surface of the central member 145, and past an inwardly facing surface of the central member 145 toward and/or to the buckle element 140. Accordingly, in some embodiments, the path of the elastic strap 110 and/or the elongate piece of elastic material 111 may extend around the central member 145. Other configurations are also contemplated.

In some embodiments having the second buckle element, such as those having no additional structure, no additional buckle element(s), and/or no additional clasping element(s) between the buckle element 140 and the second buckle element, a path of the elastic strap 110 and/or the elongate piece of elastic material 111 may extend outside of the second side member 144 and/or an outwardly facing surface of the second side member 144, between the second side member 144 and the central member 145, outside of and/or around an outwardly facing surface of the central member 145, and inside of the second side member 144 and/or an inwardly facing surface of the second side member 144 toward and/or to the buckle element 140. Accordingly, in some embodiments, the path of the elastic strap 110 and/or the elongate piece of elastic material 111 may extend around the second side member 144. Other configurations are also contemplated.

In some embodiments having the second buckle element, such as those having no additional structure, no additional buckle element(s), and/or no additional clasping element(s) between the buckle element 140 and the second buckle element, the first clasping element 120 and/or the non-elastic flap 122 may be configured to releasably engage the second buckle element. In some embodiments, the first clasping element 120 and/or the non-elastic flap 122 may be configured to extend through the second buckle element and fold back on itself to form the continuous loop. In some embodiments, the first clasping element 120 and/or the non-elastic flap 122 may be configured to extend inside of the first side member 143 and/or an inwardly facing surface of the first side member 143, between the first side member 143 and the central member 145, and outside of and/or around an outwardly facing surface of the first side member 143. Accordingly, in some embodiments, the first clasping element 120 and/or the non-elastic flap 122 may be configured to extend around the first side member 143. Other configurations are also contemplated.

Figure 7:
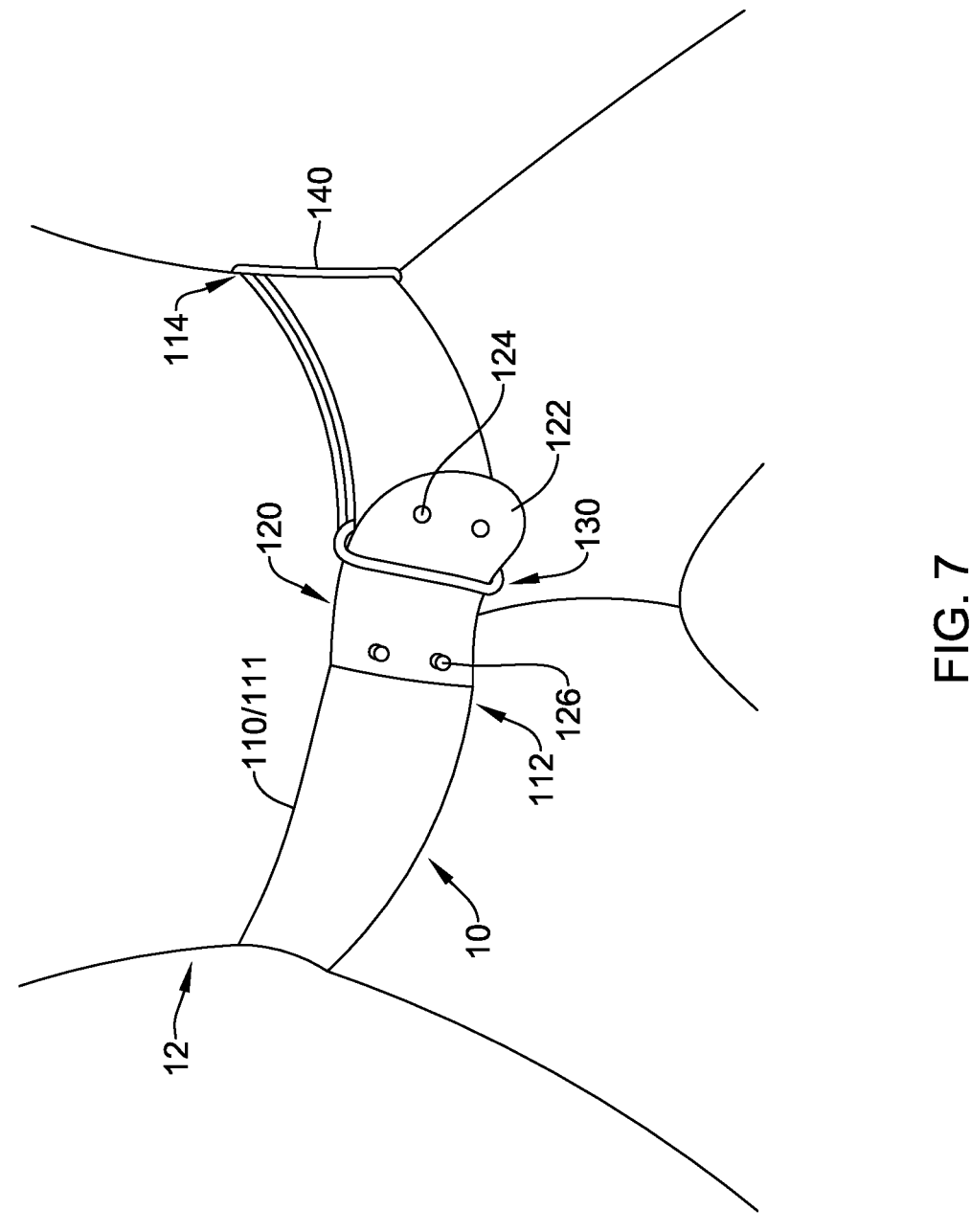
FIGS. 7-15 illustrate selected aspects related to using the back support device of FIGS. 1-6.
Figure 8:
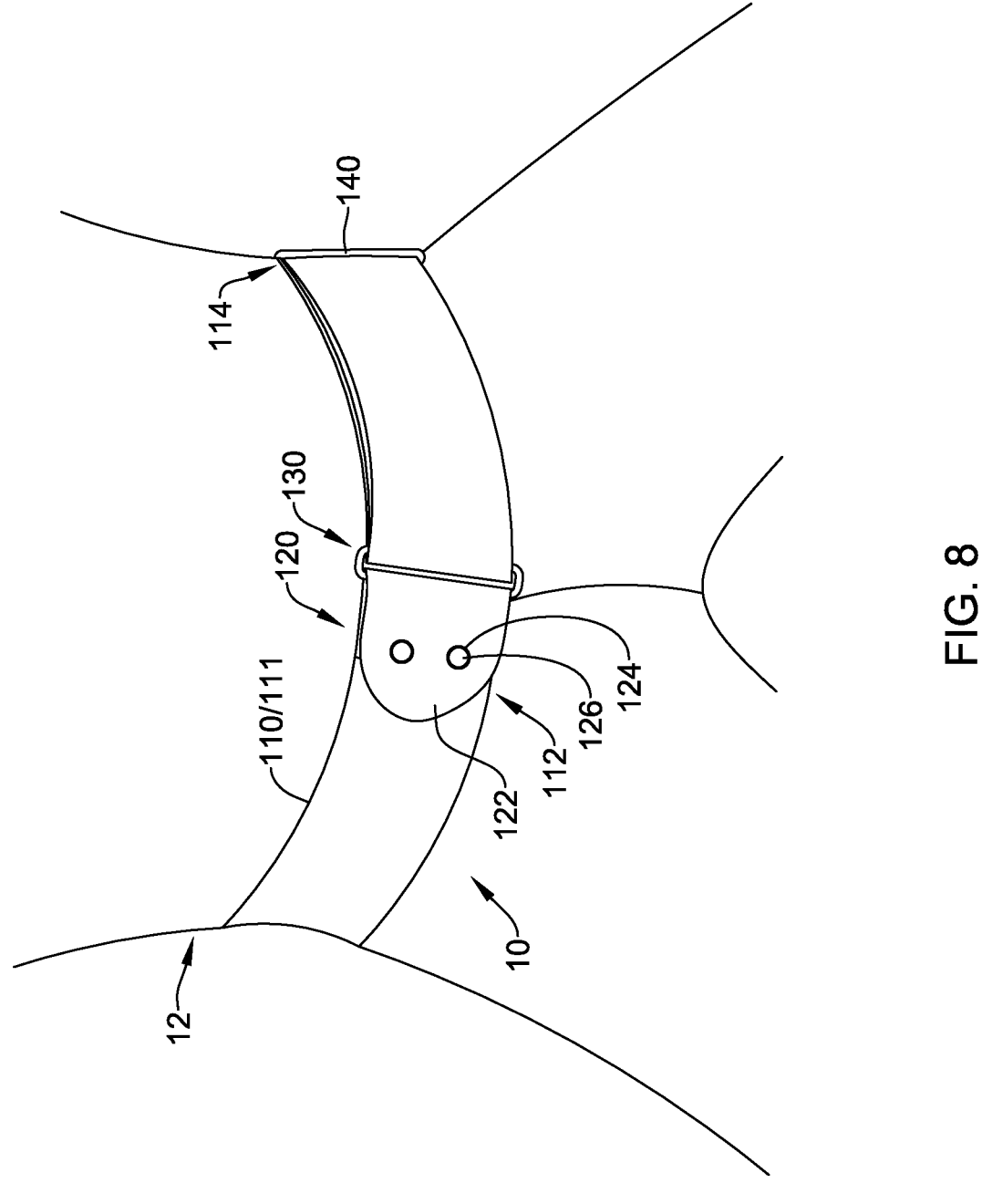

FIGS. 7-15 illustrate selected aspects of the back support device 100 and a method of supporting a lower back 12 of a user. In some embodiments, the method may include positioning the elastic strap 110 and/or the elongate piece of elastic material 111 around a torso 10 and/or the lower back 12 of the user, as seen in FIG. 7. The method may further include releasably securing the first clasping element 120 attached to the first end 112 of the elastic strap 110 and/or the elongate piece of elastic material 111 to the second clasping element 130 slidably disposed over the elastic strap 110 and/or the elongate piece of elastic material 111 to form a continuous loop around the torso 10 and/or the lower back 12 of the user, as seen in FIG. 8.

In some embodiments, positioning the elastic strap 110 and/or the elongate piece of elastic material 111 around the torso 10 and/or the lower back 12 of the user may include inserting, advancing, and/or feeding the non-elastic flap 122 of the first clasping element 120 through the closed loop of the second clasping element 130, as seen in FIG. 7. In some embodiments, releasably securing the first clasping element 120 to the second clasping element 130 may include inserting the projecting element 126 through the aperture 124 formed in the non-elastic flap 122 of the first clasping element 120, as shown in FIG. 8. In some embodiments, releasably securing the first clasping element 120 to the second clasping element 130 may include urging the non-elastic flap 122 and/or the aperture 124 formed therein over and/or on to the projecting element 126.

Figure 9:
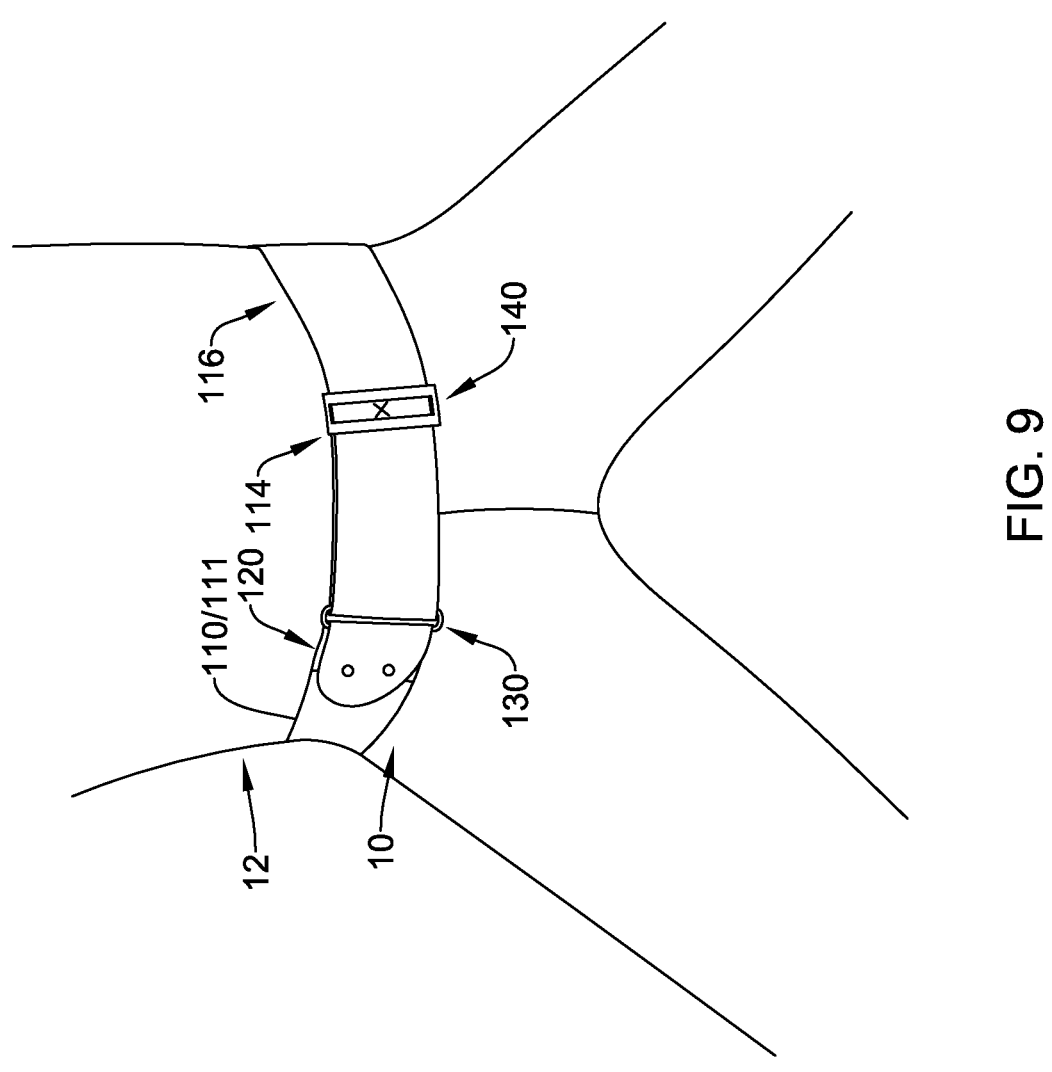

In some embodiments, the method may include sliding the buckle element 140 along the medial portion 116 of the elastic strap 110 and/or the elongate piece of elastic material 111 to secure the continuous loop around the torso 10 and/or the lower back 12 of the user such that the continuous loop holds itself in place on the torso 10 of the user in a first position, as seen in FIG. 9. The buckle element 140 may be disposed at the buckle position (marked with an "X" on the elastic strap 110 and/or the elongate piece of elastic material 111) in the first position. The continuous loop may have a first perimeter length P1 (e.g., FIG. 10) in the first position. In at least some embodiments, the continuous loop radially and/or elastically constricts upon the torso 10 of the user in the first position. In some embodiments, the continuous loop exerts a radially inward force on the torso 10 of the user in the first position.

Figure 10:
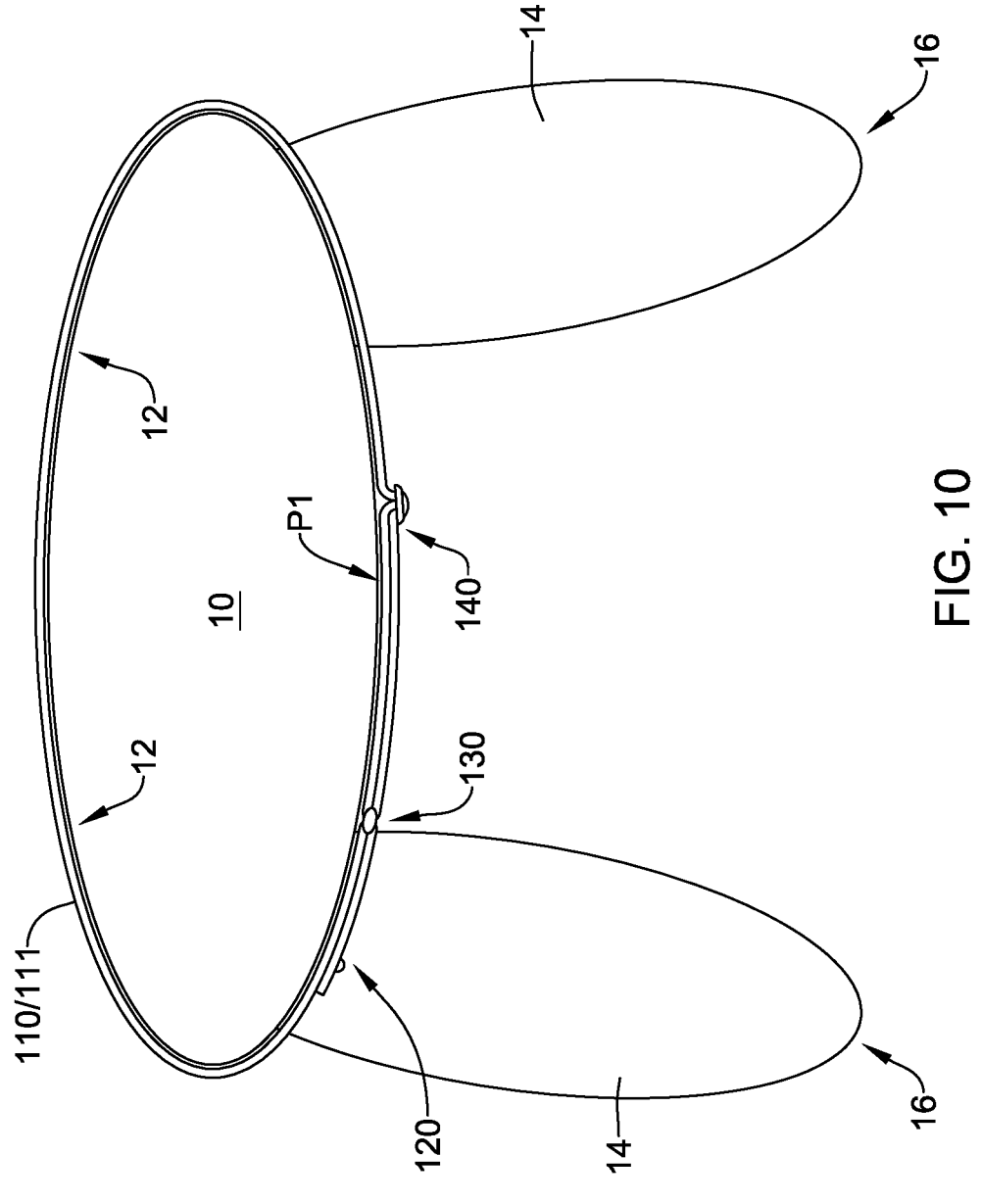

FIG. 10 schematically illustrates a top view of the user in a seated position with the continuous loop shown in the first position. In the top view shown, the torso 10 of the user may be seen as an oval. The user's leg(s) 14 extends away from the torso 10 opposite the lower back 12 to the knee(s) 16. The first perimeter length P1 may be seen and/or defined by an inwardly facing surface of the continuous loop and/or the elastic strap 110 and/or the elongate piece of elastic material 111. In the first position, there may be substantially no or very limited space between the torso 10 and the continuous loop and/or the elastic strap 110 and/or the elongate piece of elastic material 111. Gaps between the torso 10 and the continuous loop shown in FIG. 10 are merely for clarity and may not be present when the back support device 100 is disposed around the torso 10 of the user in the first position.

In some embodiments, the back support device 100 and/or the continuous loop may be adjustable. In some embodiments, the continuous loop may be adjustable in the first position. In some embodiments, the method may include sliding the buckle element 140 along the medial portion 116 of the elastic strap 110 and/or the elongate piece of elastic material 111 in a first direction toward the second clasping element 130 (e.g., to the left in FIG. 10) to loosen and/or to increase the first perimeter length P1. In some embodiments, the method may include sliding the buckle element 140 along the medial portion 116 of the elastic strap 110 and/or the elongate piece of elastic material 111 in a second direction away from the second clasping element 130 (e.g., to the right in FIG. 10) to decrease the first perimeter length P1.

Since the continuous loop may be configured to elastically constrict upon the torso 10 of the user in the first position, in some embodiments, the user may wish to adjust the first perimeter length P1 for comfort in the first position. In general, in the first position, the continuous loop and/or the elastic strap 110 and/or the elongate piece of elastic material 111 may be secured around the torso 10 of the user and the first perimeter length P1 adjusted such that the continuous loop holds itself in place on the torso 10 of the user. Generally, it is undesirable for the continuous loop and/or the first perimeter length P1 to be so large that the continuous loop falls off of the torso 10 of the user if and/or when the user stands up. It is desirable for the continuous loop to remain in place on and/or around the torso 10 of the user for convenience and/or safety. For example, if the user gets up to walk to another location, the continuous loop will remain in place on the torso 10 of the user instead of slipping down around the user's legs, which may cause a tripping hazard. Other benefits are also contemplated. As such, the continuous loop may be configured to fit snugly against the torso 10 of the user in the first position to maintain and/or hold itself in place on the torso 10 of the user.

Figure 11:
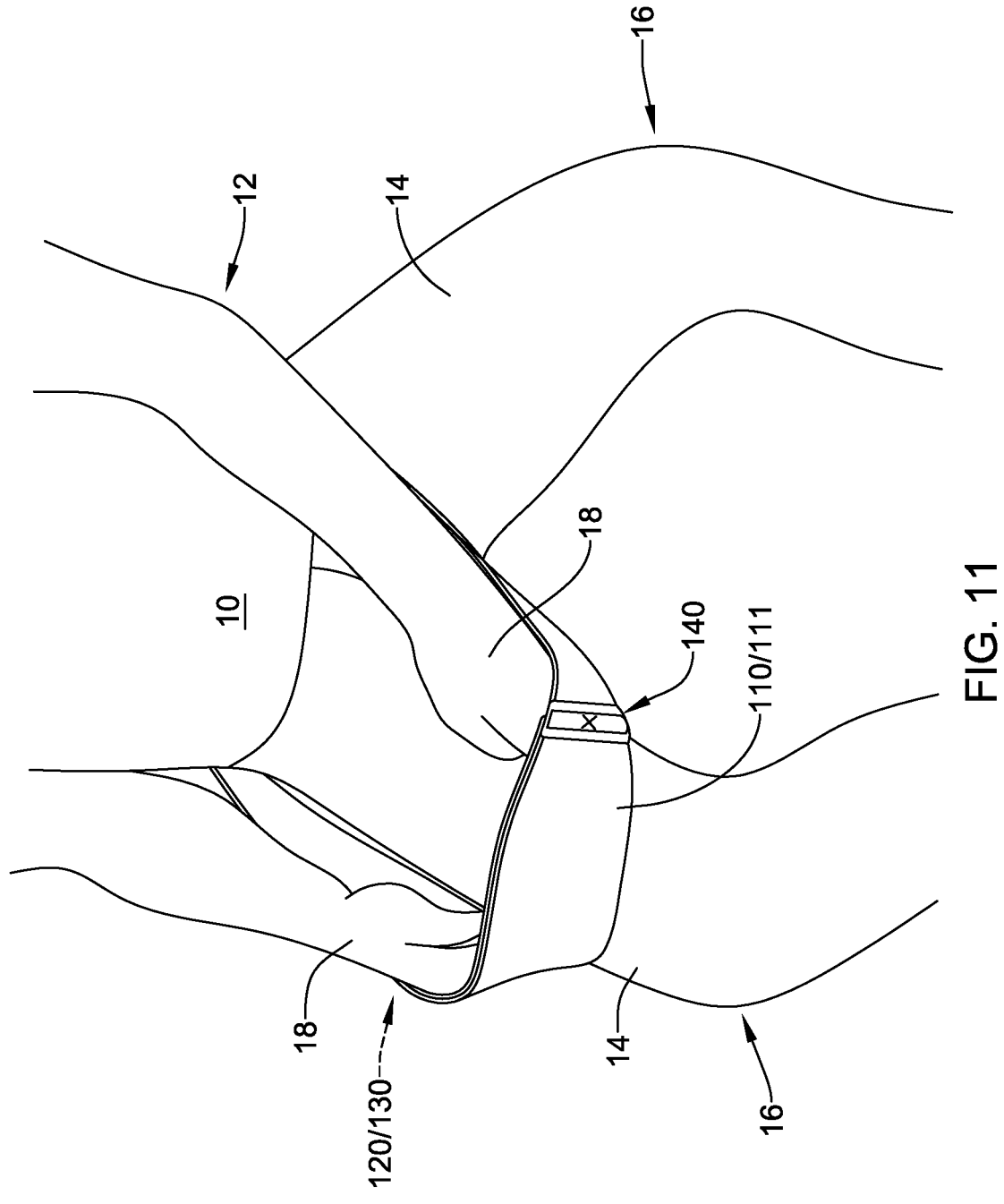
Figure 12:
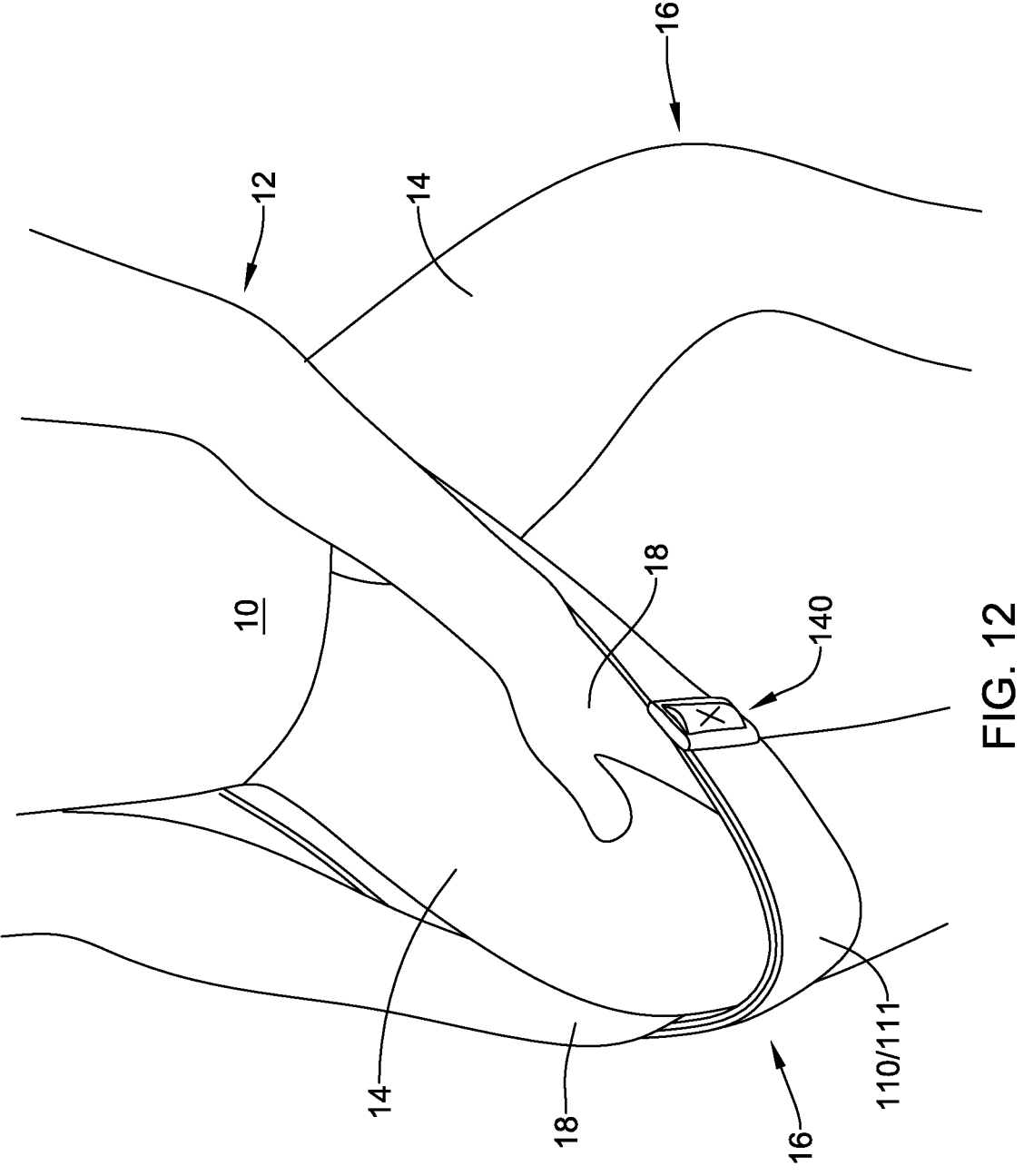
Figure 13:
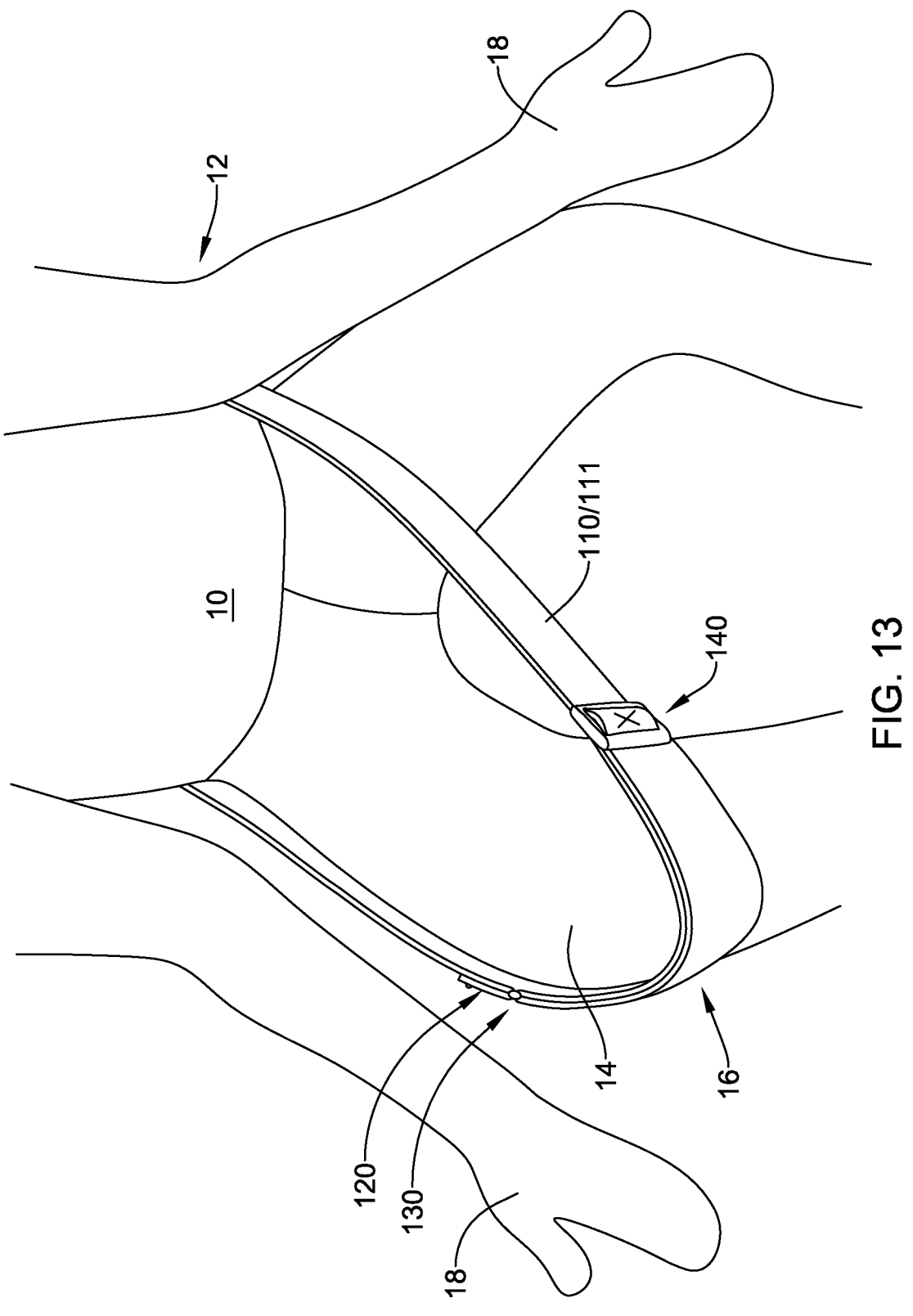
Figure 14:
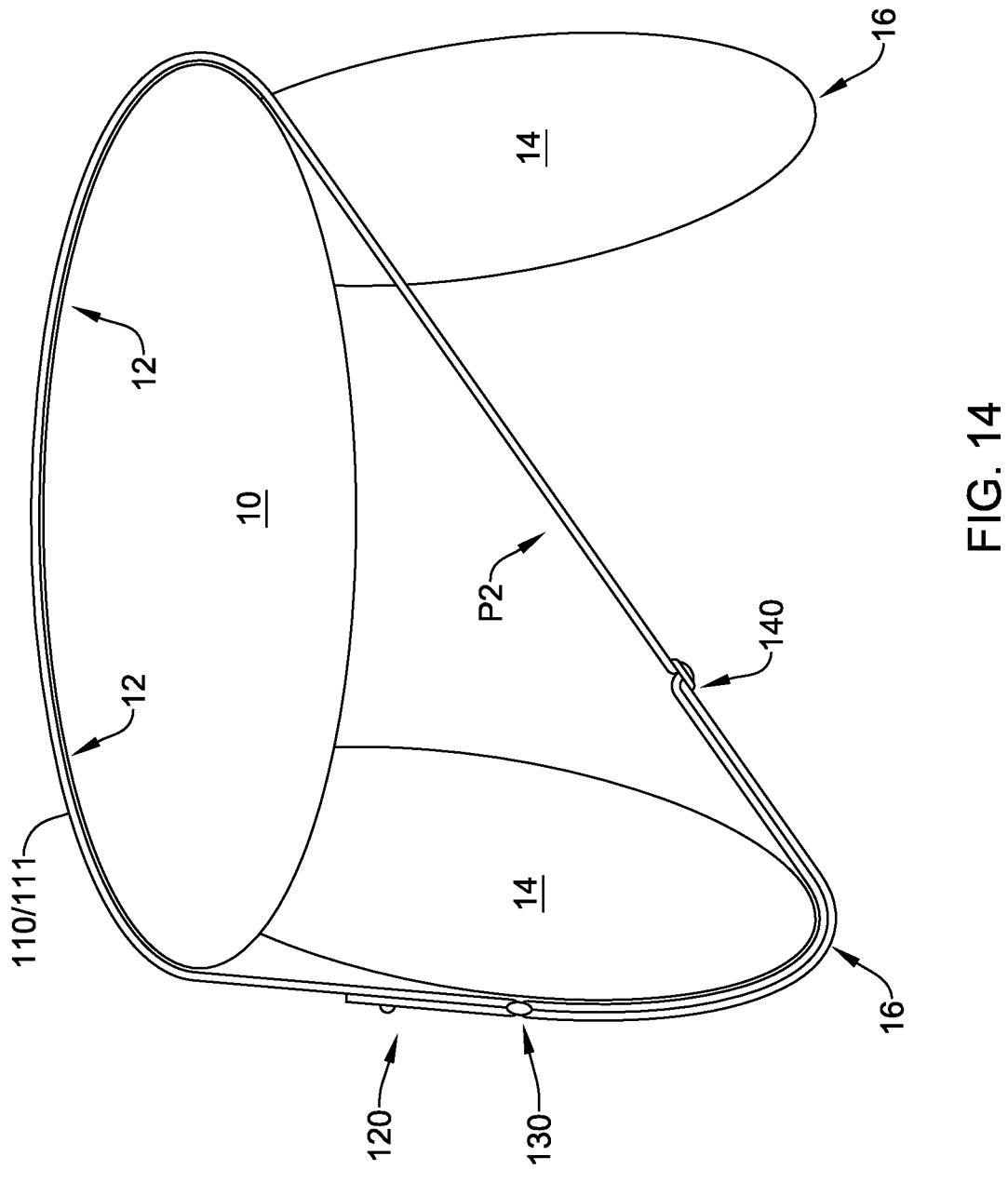
Figure 14A:
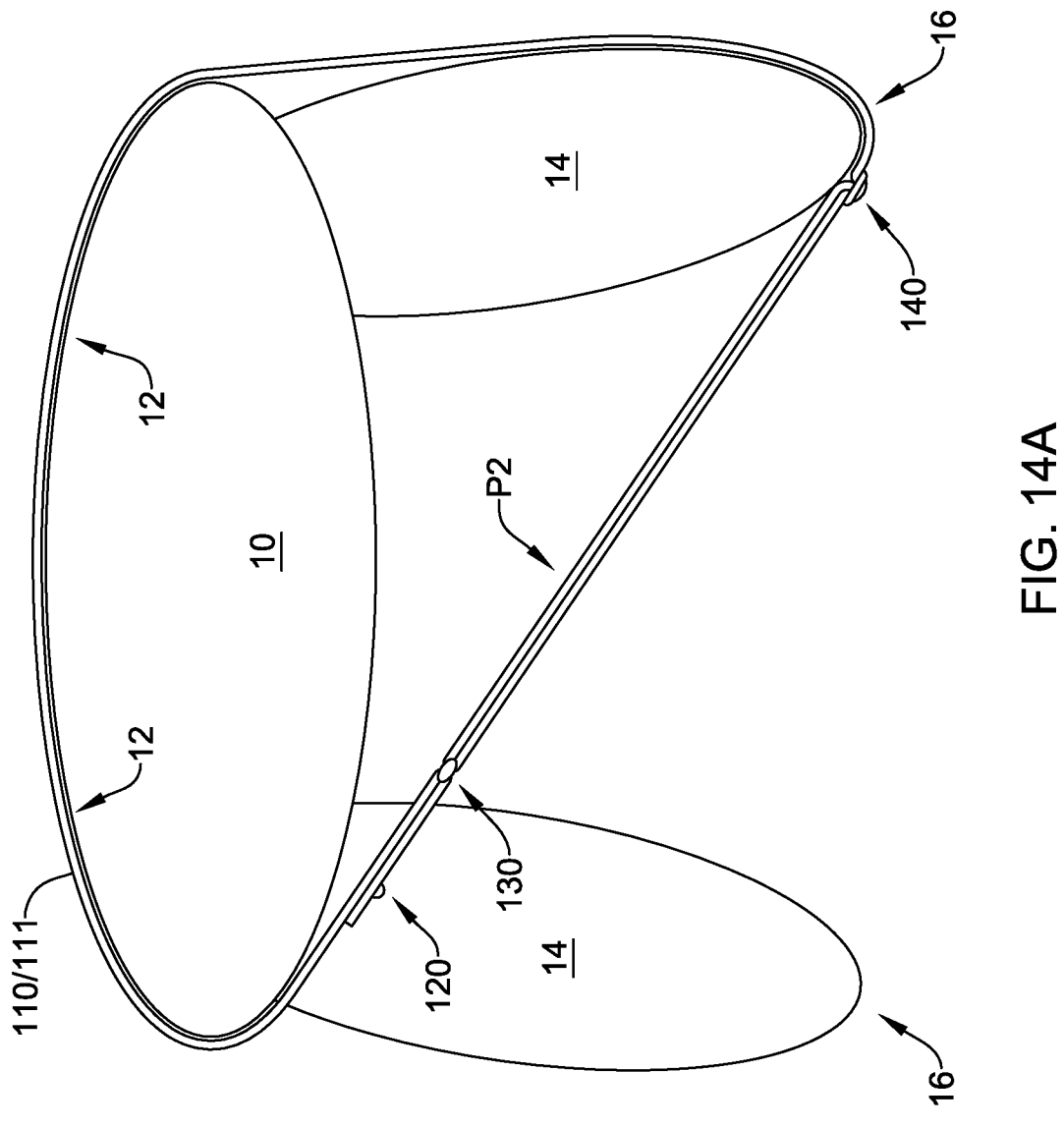

As seen in FIGS. 11-13, in some embodiments, the back support device 100 and/or the continuous loop may be movable between the first position in which the continuous loop has the first perimeter length P1 (e.g., FIG. 10) and a second position in which the continuous loop has a second perimeter length P2 (e.g., FIGS. 14-15) via elastic elongation. The back support device 100 and/or the continuous loop may be movable, without changing the buckle position between the first position, in which the back support device 100 forms a continuous loop extending around and elastically constricting upon the torso 10 of the user, and the second position, in which the continuous loop extends around the lower back 12 of the user and at least one knee 16 of the user, as seen in FIGS. 14-14A. The at least one knee 16 may be the user's right knee, as shown in FIG. 14, or the user's left knee, as shown in FIG. 14A. In some embodiments, positioning the continuous loop around the left knee of the user may be a preferred configuration and/or use of the back support device 100. In one non-limiting example, the continuous loop may be positioned around the lower back 12 of the user and the left knee of the user to use the back support device 100 while driving. Other configurations are also contemplated. In some embodiments, the continuous loop may be moved from the right knee to the left knee, or from the left knee to the right knee, during use as desired for user comfort.

Figure 15:
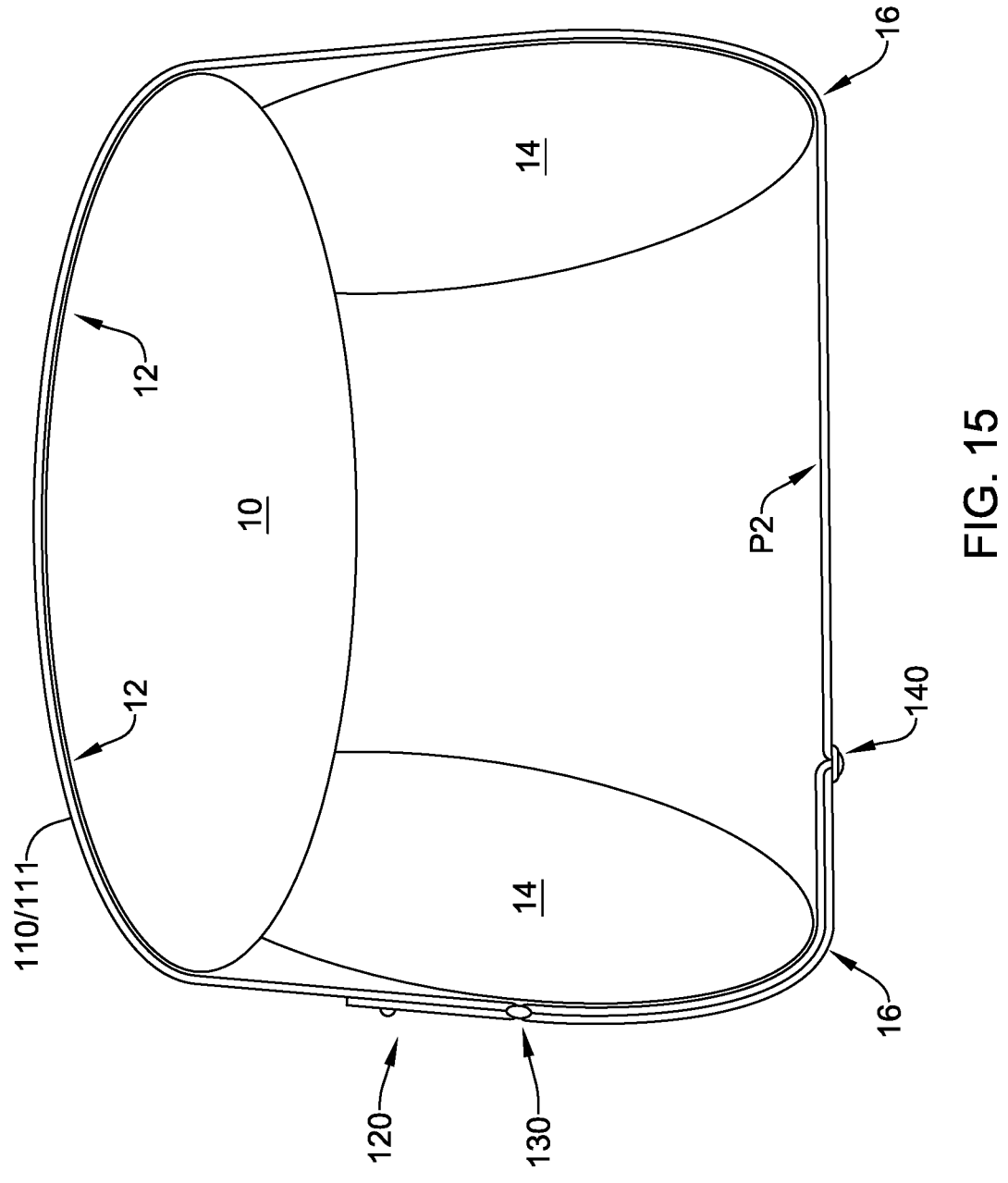

In some embodiments, in the second position, the continuous loop may extend around the lower back 12 of the user and two knees of the user, as seen in FIG. 15. In some embodiments, positioning the continuous loop around two knees may increase the radially inward force applied against the lower back 12 of the user compared to positioning the continuous loop around one knee. This may be useful if the user wants a temporary increase in the radially inward force (e.g., the amount of support) against the lower back 12 of the user without adjusting the buckle position of the buckle element 140.

In some embodiments, the second perimeter length P2 may be greater than the first perimeter length P1. In some embodiments, the first perimeter length P1 may be less than the second perimeter length P2. In some embodiments, a single or one continuous loop may extend around at least one knee 16 or around two knees. Two separate loops are not required in order to position or extend the back support device 100 around two knees (e.g., the back support device does not require separate loops for each knee).

In use, to move the back support device 100 and/or the continuous loop from the first position (e.g., FIGS. 9-10) to the second position (e.g., FIGS. 13-15), the user may insert their hands 18 inside of the continuous loop in the first position. The back support device 100 and/or the continuous loop may then be stretched away from the torso 10 of the user with the hands 18 and towards the at least one knee 16 of the user, as seen in FIG. 11. Note that in FIG. 11 the "X" on the elastic strap 110 and/or the elongate piece of elastic material 111 marking the buckle position remains in the same position relative to the buckle element 140 as it was in FIG. 9. This is because the buckle element 140 remains in a fixed position along the elastic strap 110 and/or the elongate piece of elastic material 111 as the elastic strap 110 and/or the elongate piece of elastic material 111 is elastically stretched and/or elongated.

After urging the elastic strap 110 and/or the elongate piece of elastic material 111 away from the torso 10 and over the at least one knee 16, the user's hands 18 are used to position the elastic strap 110 and/or the elongate piece of elastic material 111 on the bump located at the top of the user's shin in the second position, as shown in FIG. 12. Then the user's hands 18 may be removed from behind the elastic strap 110 and/or the elongate piece of elastic material 111, as shown in FIG. 13. In some embodiments, if desired, the user may vary the amount of pressure the continuous loop and/or the elastic strap 110 and/or the elongate piece of elastic material 111 puts on the at least one knee 16 and/or the shin(s) by spreading apart the overlapping medial portions of the elastic strap 110 and/or the elongate piece of elastic material 111 to spread out the pressure on the at least one knee 16 and/or the shin(s). In some embodiments, if desired, the user may vary the amount of pressure the continuous loop and/or the elastic strap 110 and/or the elongate piece of elastic material 111 puts on the at least one knee 16 and/or the shin(s) by changing which knee the continuous loop and/or the elastic strap 110 and/or the elongate piece of elastic material 111 extends around (e.g., moving the elastic strap 110 and/or the elongate piece of elastic material 111 from the left knee to the right knee, or vice versa).

Accordingly, in some embodiments, the method of supporting the lower back 12 of the user may include moving the continuous loop and/or the elastic strap 110 and/or the elongate piece of elastic material 111 from the first position to the second position in which the continuous loop extends around the lower back 12 of the user and at least one knee 16 of the user. In some embodiments, the elastic strap 110 and/or the elongate piece of elastic material 111 elastically elongates from the first position to the second position such that in the second position the continuous loop has a second perimeter length P2 greater than the first perimeter length P1. In some embodiments, moving the continuous loop and/or the elastic strap 110 and/or the elongate piece of elastic material 111 from the first position to the second position may require no adjustment. For example, in some embodiments, the back support device 100 and/or the continuous loop is movable between the first position and the second position only via elasticity of the elastic strap 110 and/or the elongate piece of elastic material 111. No other structure of the back support device 100 needs to be moved or adjusted in order to move the back support device 100 and/or the continuous loop between the first position and the second position. For example, the back support device 100 and/or the continuous loop is movable without moving the buckle element 140 and/or without changing the buckle position.

In some embodiments, the method may include moving the back support device 100 and/or the continuous loop from the second position to the first position. In some embodiments, the method may include moving the back support device 100 and/or the continuous loop from the second position to the first position without any adjustment other than elastic contraction. In some embodiments, the method may include moving the back support device 100 and/or the continuous loop from the second position to the first position without moving the buckle element 140 and/or without changing the buckle position.

In some embodiments, the method may include sliding the buckle element 140 along the medial portion 116 of the elastic strap 110 and/or the elongate piece of elastic material 111 in the first position to change the buckle position. In some embodiments, the method may include sliding the buckle element 140 along the medial portion 116 of the elastic strap 110 and/or the elongate piece of elastic material 111 to change in inward force exerted by the continuous loop against the lower back 12 of the user in the second position. In one example, sliding the buckle element 140 toward the second clasping element 130 may loosen the continuous loop in the first position such that less elastic elongation is required to move the continuous loop to the second position, which will in turn reduce the inward force exerted by the continuous loop against the lower back 12 of the user in the second position. In another example, sliding the buckle element 140 away from the second clasping element 130 may tighten the continuous loop in the first position such that more elastic elongation is required to move the continuous loop to the second position, which will in turn increase the inward force exerted by the continuous loop against the lower back 12 of the user in the second position. The user may make these adjustments to satisfy comfort and/or support needs. Other configurations and/or adjustments are also contemplated.

Figure 16:
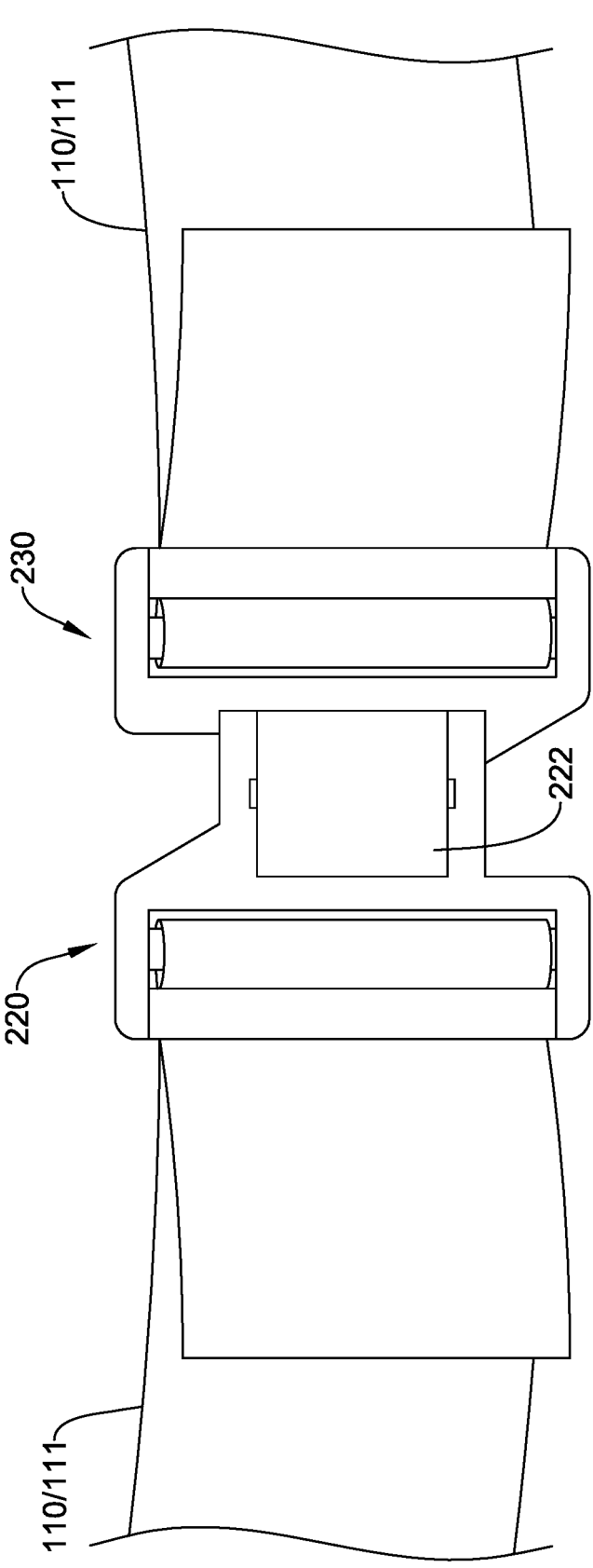
FIGS. 16-17 illustrate selected aspects of an alternative clasping mechanism.
Figure 17:
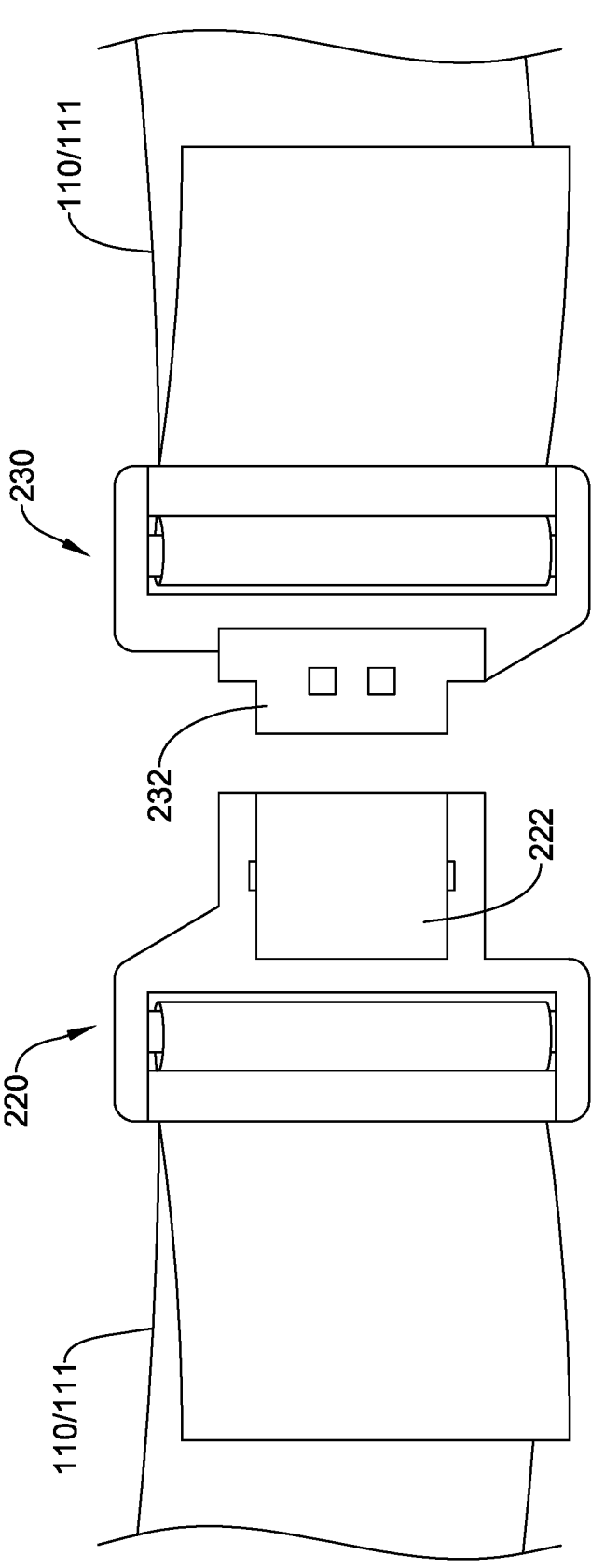
Figure 18:
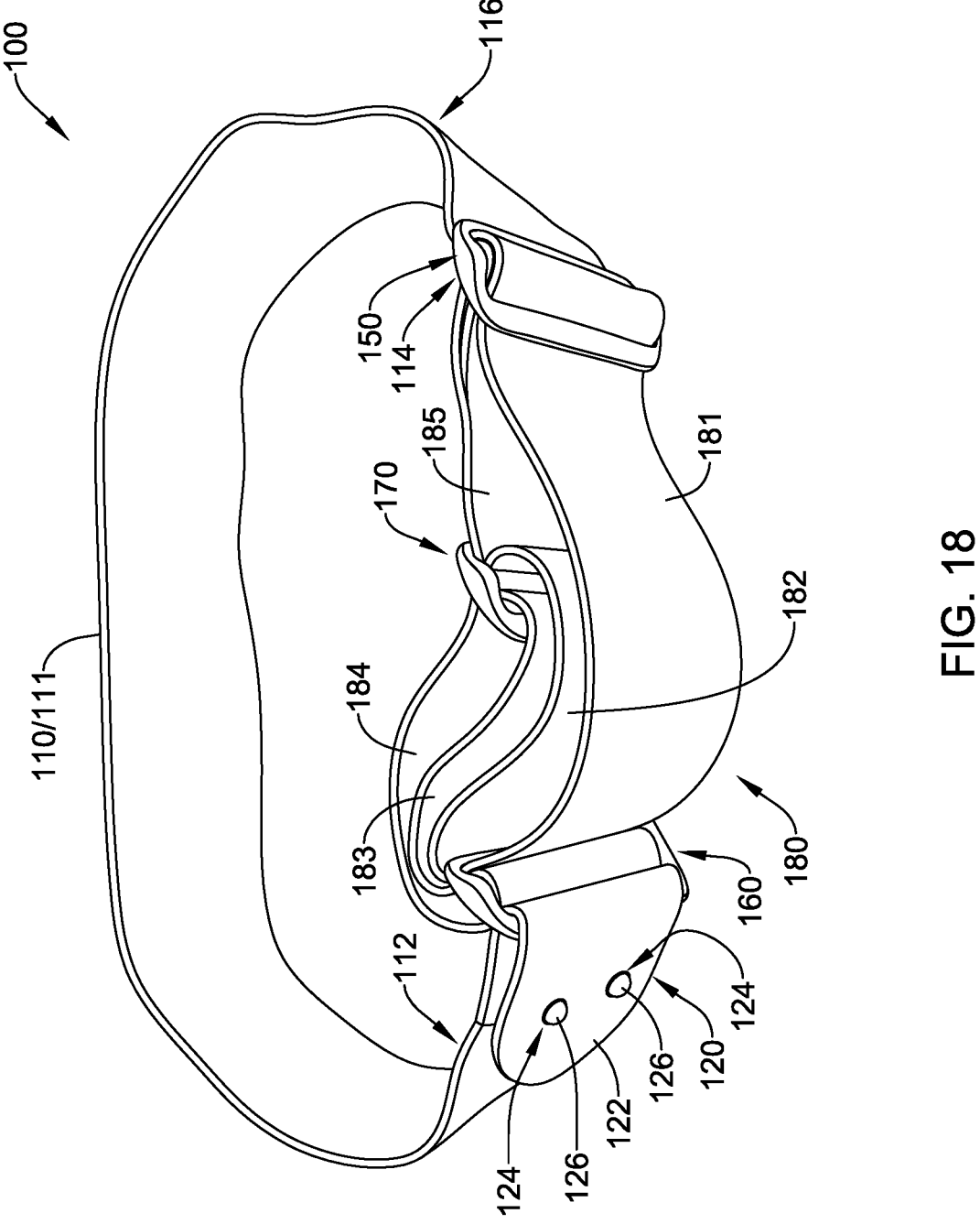
FIGS. 18-20A illustrates selected aspects of a back support device according to the disclosure.
Figure 19:
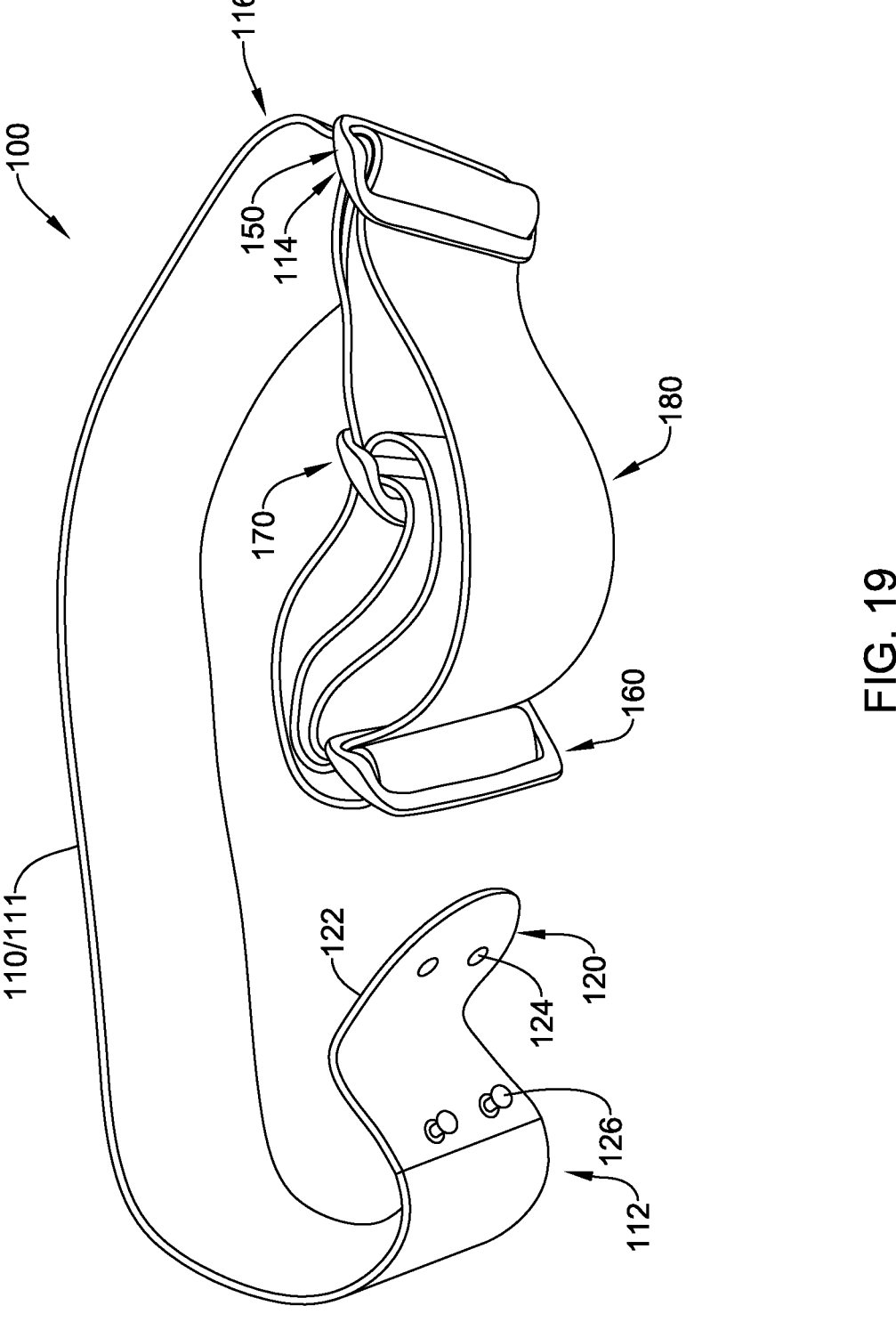

In some alternative embodiments, the back support device may include an alternative clasping mechanism. For example, the alternative clasping mechanism may include a quick release mechanism. In some embodiments, the back support device may include a first clasping element 220 secured to the elastic strap 110 and/or the elongate piece of elastic material 111 and a second clasping element 230 secured to the elastic strap 110 and/or the elongate piece of elastic material 111. The first clasping element 220 may be configured to releasably engage with the second clasping element 230, as shown in FIGS. 16-17. In one example, the first clasping element 220 may include a button 222 configured to rock and/or tilt within the first clasping element 220. In an open position, the button 222 may be configured to receive and/or accept a tongue portion 232 of the second clasping element 230. In a closed position, the button 222 may be configured to secure and/or lock the tongue portion 232 of the second clasping element 230 within and/or relative to the first clasping element 220. Other clasping mechanisms and/or configurations thereof are also contemplated.

In some embodiments, the first clasping element 220 and/or the second clasping element 230 may permit adjustment of the length of the elastic strap 110 and/or the elongate piece of elastic material 111. In some embodiments, the first clasping element 220 and/or the second clasping element 230 may engage the elastic strap 110 and/or the elongate piece of elastic material 111 in a ladder-lock manner to secure the elastic strap 110 and/or the elongate piece of elastic material 111 in place relative to the first clasping element 220 and/or the second clasping element 230 while permitting easy adjustment of the length of the elastic strap 110 and/or the elongate piece of elastic material 111 and/or the positioning of the first clasping element 220 and/or the second clasping element 230.

In some embodiments, the first end of the elastic strap 110 and/or the elongate piece of elastic material 111 may be secured to a first buckle element, similar to the buckle element 140 above, the medial portion of the elastic strap 110 and/or the elongate piece of elastic material 111 may pass through the first clasping element 220 similar to the second clasping element 130 above, and the second end of the elastic strap 110 and/or the elongate piece of elastic material 111 may be fixedly secured to the second clasping element 230. In some embodiments, the first end of the elastic strap 110 and/or the elongate piece of elastic material 111 may be fixedly secured to the first clasping element 220, the medial portion of the elastic strap 110 and/or the elongate piece of elastic material 111 may pass through the second clasping element 230 similar to the second clasping element 130 above, and the second end of the elastic strap 110 and/or the elongate piece of elastic material 111 may be secured to a second buckle element, similar to the buckle element 140 above. In some embodiments, the first end of the elastic strap 110 and/or the elongate piece of elastic material 111 may be secured to a first buckle element, similar to the buckle element 140 above, the medial portion of the elastic strap 110 and/or the elongate piece of elastic material 111 may pass through the first clasping element 220 and the second clasping element 230 similar to the second clasping element 130 above, and the second end of the elastic strap 110 and/or the elongate piece of elastic material 111 may be secured to a second buckle element, similar to the buckle element 140 above. In each of the above examples, the first buckle element and/or the second buckle element may be constructed and/or may function substantially similar to the buckle element 140 described herein.

FIGS. 18-20A illustrate selected aspects of an example configuration of the back support device 100 discussed herein. In some embodiments, the back support device 100 may include the elastic strap 110, the first clasping element 120 attached to the first end 112 of the elastic strap 110, and a first buckle element 150 secured to the second end 114 of the elastic strap 110 and slidably disposed over the medial portion 116 of the elastic strap 110. The back support device 100 may include a second buckle element 160 slidably disposed over the elastic strap 110 and configured to releasably engage the first clasping element 120 to form the continuous loop. In some embodiments, the back support device 100 may include a third buckle element 170 slidably disposed over the elastic strap 110 between the first buckle element 150 and the second buckle element 160.

In some embodiments, the first buckle element 150, the second buckle element 160, and/or the third buckle element 170 may be identical in structure, form, and/or function to the buckle element 140 described herein. Accordingly, such description is not repeated and individual features, elements, and/or components of the first buckle element 150, the second buckle element 160, and/or the third buckle element 170, where described, may be referred to using the reference numbers assigned above with respect to the buckle element 140 shown in FIGS. 5-6 (e.g., the first end member 141, the second end member 142, the first side member 143, the second side member 144, the central member 145, etc.) in the interest of brevity. The use of these reference numbers is not intended to be limiting and is merely meant to enhance understanding.

In some embodiments, the elastic strap 110 may include a plurality of segments 180 arranged and/or positioned in an overlapping manner. In some embodiments, the plurality of segments 180 of the elastic strap 110 may be defined by the first buckle element 150, the second buckle element 160, and the third buckle element 170. The plurality of segments 180 may circumferentially overlap between the first buckle element 150 and the second buckle element 160. In at least some embodiments, the plurality of segments 180 may form a back-and-forth path of the elastic strap 110 (when viewed from above or below) between the first buckle element 150 and the second buckle element 160.

In some embodiments, the plurality of segments 180 may include a first segment 181 extending between the first buckle element 150 and the second buckle element 160, a second segment 182 extending between the second buckle element 160 and the third buckle element 170, a third segment 183 extending between the third buckle element 170 and the second buckle element 160, a fourth segment 184 extending between the second buckle element 160 and the third buckle element 170, and/or a fifth segment 185 extending between the third buckle element 170 and the first buckle element 150. Other configurations and/or arrangements including more segments or fewer segments are also contemplated. It shall be understood that each segment of the plurality of segments 180 may be defined and/or delineated by identifiable structure (e.g., the buckle elements) found in the back support device 100 (e.g., the first buckle element 150, the second buckle element 160, and/or the third buckle element 170, and/or any additional buckle elements, where present).

For the purpose of discussion, the continuous loop shall be considered to extend circumferentially around and/or to surround a central axis. The first segment 181 of the plurality of segments 180 may be disposed radially outward of all other segments of the plurality of segments 180 with respect to the central axis. The second segment 182 may be disposed radially inward of the first segment 181, the third segment 183 may be disposed radially inward of the second segment 182, and the fourth segment 184 may be disposed radially inward of the third segment 183. The fifth segment 185 may be disposed radially inward of the first segment 181. In some embodiments, the fifth segment 185 may be circumferentially offset from the fourth segment 184, the third segment 183, and/or the second segment 182. In some embodiments, the fifth segment 185 may be circumferentially aligned with the fourth segment 184.

The back-and-forth path of the elastic strap 110 formed by the plurality of segments 180 will now be described with directional references made with respect to the central axis of the continuous loop as viewed from above along the central axis and/or from the front viewing toward the central axis. In at least some embodiments, the back-and-forth path of the elastic strap 110 formed by the plurality of segments 180 may extend from the first buckle element 150 clockwise to the second buckle element 160, over an outwardly facing surface of the second side member 144 of the second buckle element 160, between the second side member 144 and the central member 145 of the second buckle element 160, behind an inwardly facing surface of the second side member 144 of the second buckle element 160 (e.g., around the second side member 144 of the second buckle element 160), counterclockwise to the third buckle element 170 radially inward of the first segment 181, over an outwardly facing surface of the central member 145 of the third buckle element 170, between the central member 145 and the second side member 144 of the third buckle element 170, behind an inwardly facing surface of the central member 145 of the third buckle element 170, between the central member 145 and the first side member 143 of the third buckle element 170 (e.g., around the central member 145 of the third buckle element 170), over an outwardly facing surface of the first side member 143 of the third buckle element 170, clockwise to the second buckle element 160 radially inward of the second segment 182, behind the inwardly facing surface of the second side member 144 of the second buckle element 160, between the second side member 144 and the central member 145 of the second buckle element 160, over an outwardly facing surface of the central member 145 of the second buckle element 160, between the central member 145 and the first side member 143 of the second buckle element 160, behind an inwardly facing surface of the central member 145 of the second buckle element 160 (e.g., around the central member 145 of the second buckle element 160), counterclockwise to the third buckle element 170 radially inward of the third segment 183, behind an inwardly facing surface of the first side member 143 of the third buckle element 170, behind the inwardly facing surface of the central member 145 of the third buckle element 170, between the central member 145 and the second side member 144 of the third buckle element 170, over an outwardly facing surface of the second side member 144 of the third buckle element 170, and counterclockwise to the first buckle element 150 radially inward of the first segment 181. In some embodiments, an outwardly facing surface of the fifth segment 185 may directly face an inwardly facing surface of the first segment 181.

Figure 20:
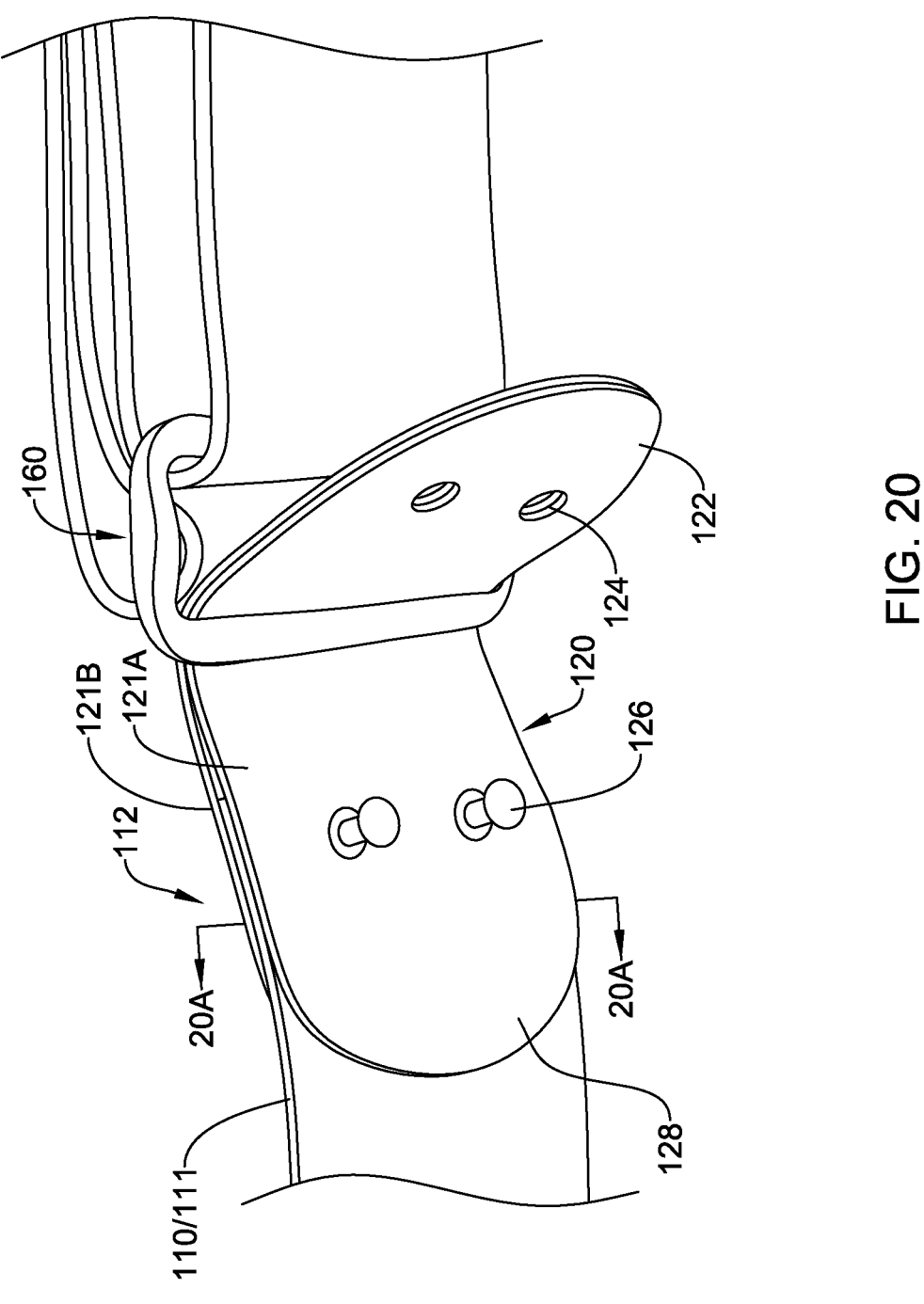
Figure 20A:
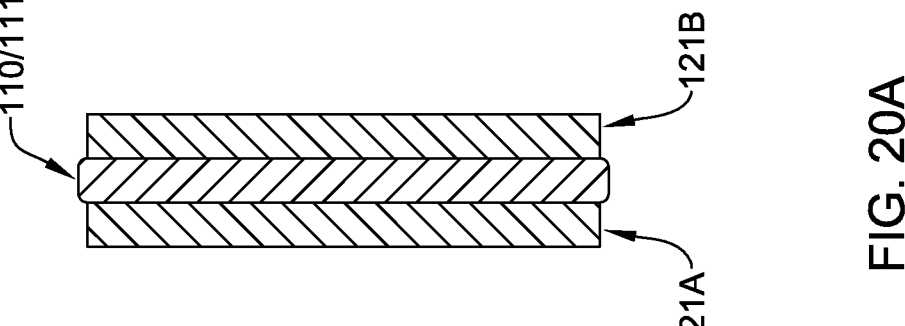

FIG. 20 illustrates selected aspects of releasably engaging the first clasping element 120 with the second buckle element 160. In some embodiments, at least a portion 128 of the first clasping element 120 and/or the non-elastic flap 122 is fixedly secured and/or fixedly attached to the first end 112 of the elastic strap 110 and/or the elongate piece of elastic material 111. In some embodiments, the first clasping element 120 and/or the non-elastic flap 122 may include a first layer 121A and a second layer 121B. In some embodiments, the first layer 121A and the second later 121B may be formed from the same material (e.g., leather, synthetic leather, other non-elastic materials, etc.). In some embodiments, the first layer 121A and the second later 121B may be formed from different materials. In some embodiments, the elastic strap 110 and/or the elongate piece of elastic material 111 may extend between the first layer 121A and the second layer 121B, as seen in FIGS. 20-20A. The at least a portion 128 of the first clasping element 120 and/or the non-elastic flap 122 may be fixedly secured and/or fixedly attached to the first end 112 of the elastic strap 110 and/or the elongate piece of elastic material 111. It shall be understood that the construction of the first clasping element 120 and/or the non-elastic flap 122 shown in FIG. 20 and/or described herein is not limited to use with the example configuration of the back support device shown in FIGS. 18-19 and may also be used in conjunction with the back support device shown in FIGS. 1-4. The reverse is also true, and the configuration shown in FIGS. 1-4 may be used with the example configuration of the back support device shown in FIGS. 18-19.

In some embodiments, the first clasping element 120 and/or the non-elastic flap 122 may be configured to extend through the second buckle element 160 and fold back on itself to form the continuous loop. In at least some embodiments, the first clasping element 120 and/or the non-elastic flap 122 may be configured to extend between the first side member 143 and the central member 145 of the second buckle element 160 (e.g., around the first side member 143 of the second buckle element 160) and fold back on itself to form the continuous loop.

FIGS. 21-26 illustrate selected aspects of the back support device 100 and a method of supporting a lower back 12 of a user. In some embodiments, the method may include positioning the elastic strap 110 and/or the elongate piece of elastic material 111 around a torso 10 and/or the lower back 12 of the user, wherein the elastic strap 110 and/or the elongate piece of elastic material 111 includes the first end 112 and the second end 114, the second end 114 being secured to the first buckle element 150 slidably disposed on the medial portion 116 of the elastic strap 110 and/or the elongate piece of elastic material 111.

Figure 21:
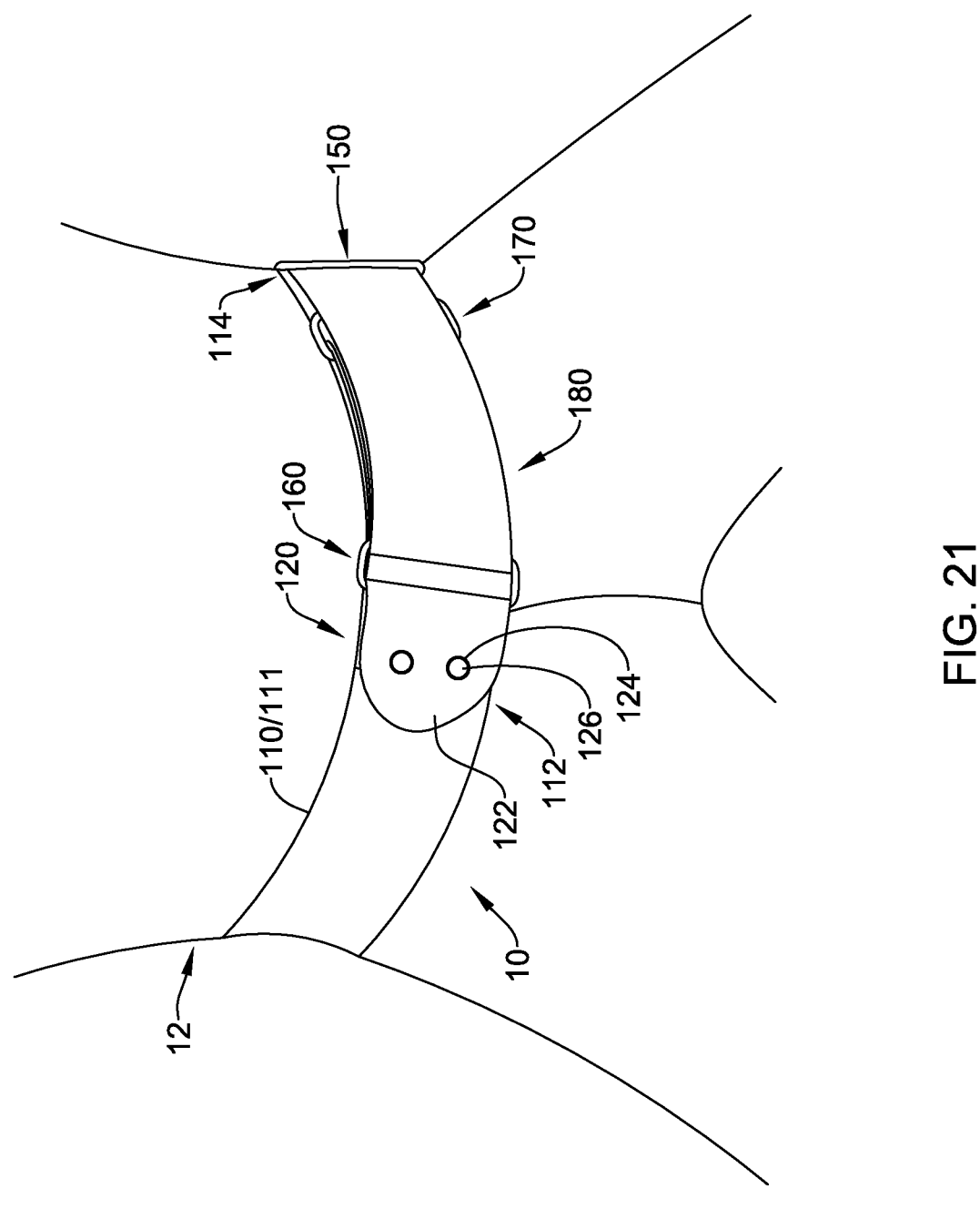
FIGS. 21-30 illustrate selected aspects related to using the back support device of FIGS. 18-20A.
Figure 22:
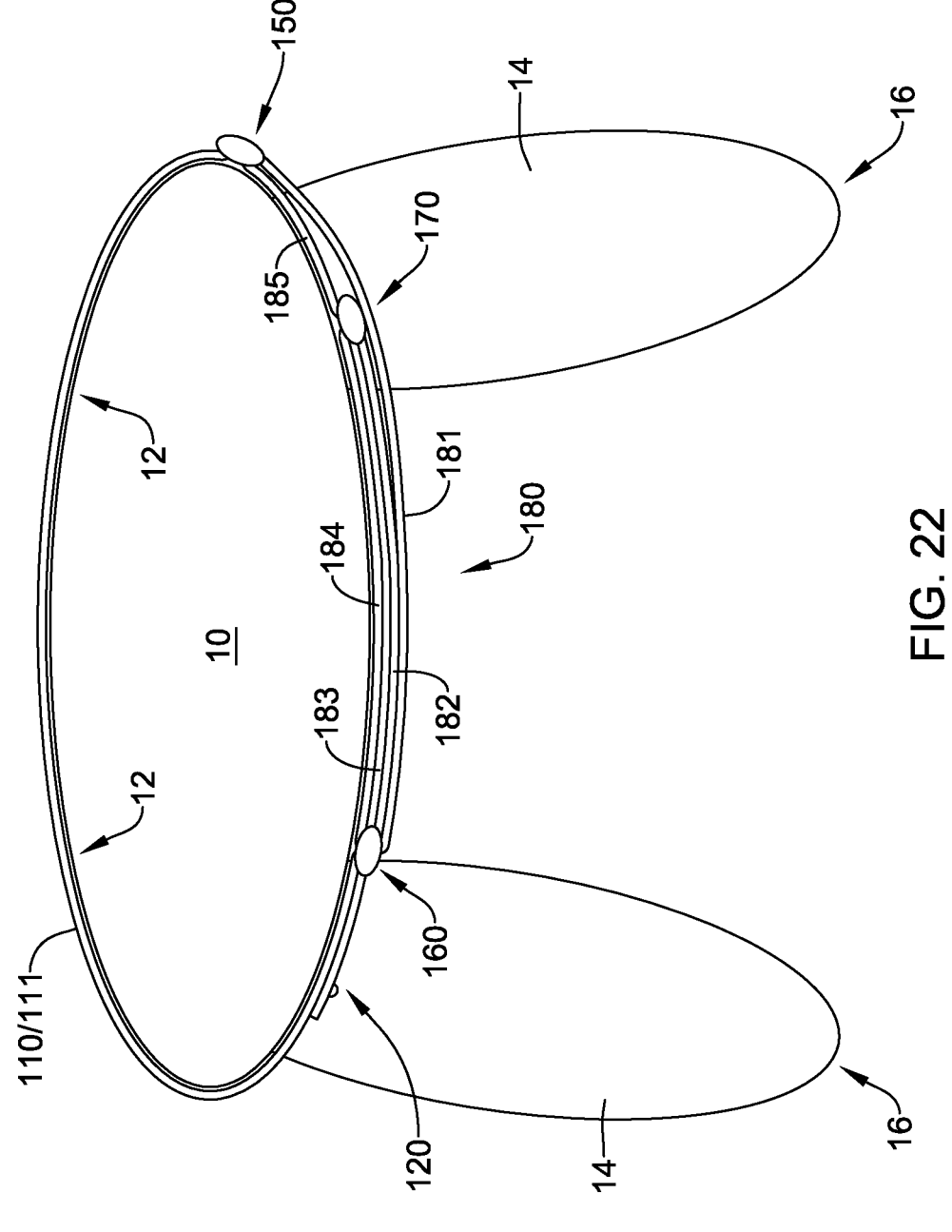

In some embodiments, the method may include releasably securing the first clasping element 120 attached to the first end 112 of the elastic strap 110 and/or the elongate piece of elastic material 111 to the second buckle element 160 slidably disposed over the elastic strap 110 and/or the elongate piece of elastic material 111 to form a continuous loop around the torso 10 and/or the lower back 12 of the user in a first position, as seen in FIGS. 21-22, wherein FIG. 22 schematically illustrates a top view of the user in a seated position with the continuous loop in the first position. In the top view shown, the torso 10 of the user may be seen as an oval. The user's leg(s) 14 extends away from the torso 10 opposite the lower back 12 to the knee(s) 16. In the first position, there may be substantially no or very limited space between the torso 10 and the continuous loop and/or the elastic strap 110 and/or the elongate piece of elastic material 111. Gaps between the torso 10 and the continuous loop shown in FIG. 22 are merely for clarity and may not be present when the back support device 100 is disposed around the torso 10 of the user in the first position.

In some embodiments, positioning the elastic strap 110 and/or the elongate piece of elastic material 111 around the torso 10 and/or the lower back 12 of the user may include inserting, advancing, and/or feeding the non-elastic flap 122 of the first clasping element 120 through the second buckle element 160 and/or around the first side member 143 of the second buckle element 160, as seen in FIG. 20. In some embodiments, releasably securing the first clasping element 120 to the second buckle element 160 may include inserting the projecting element 126 through the aperture 124 formed in the non-elastic flap 122 of the first clasping element 120, as shown in FIG. 21. In some embodiments, releasably securing the first clasping element 120 to the second buckle element 160 may include urging the non-elastic flap 122 and/or the aperture 124 formed therein over and/or on to the projecting element 126.

Figure 23:
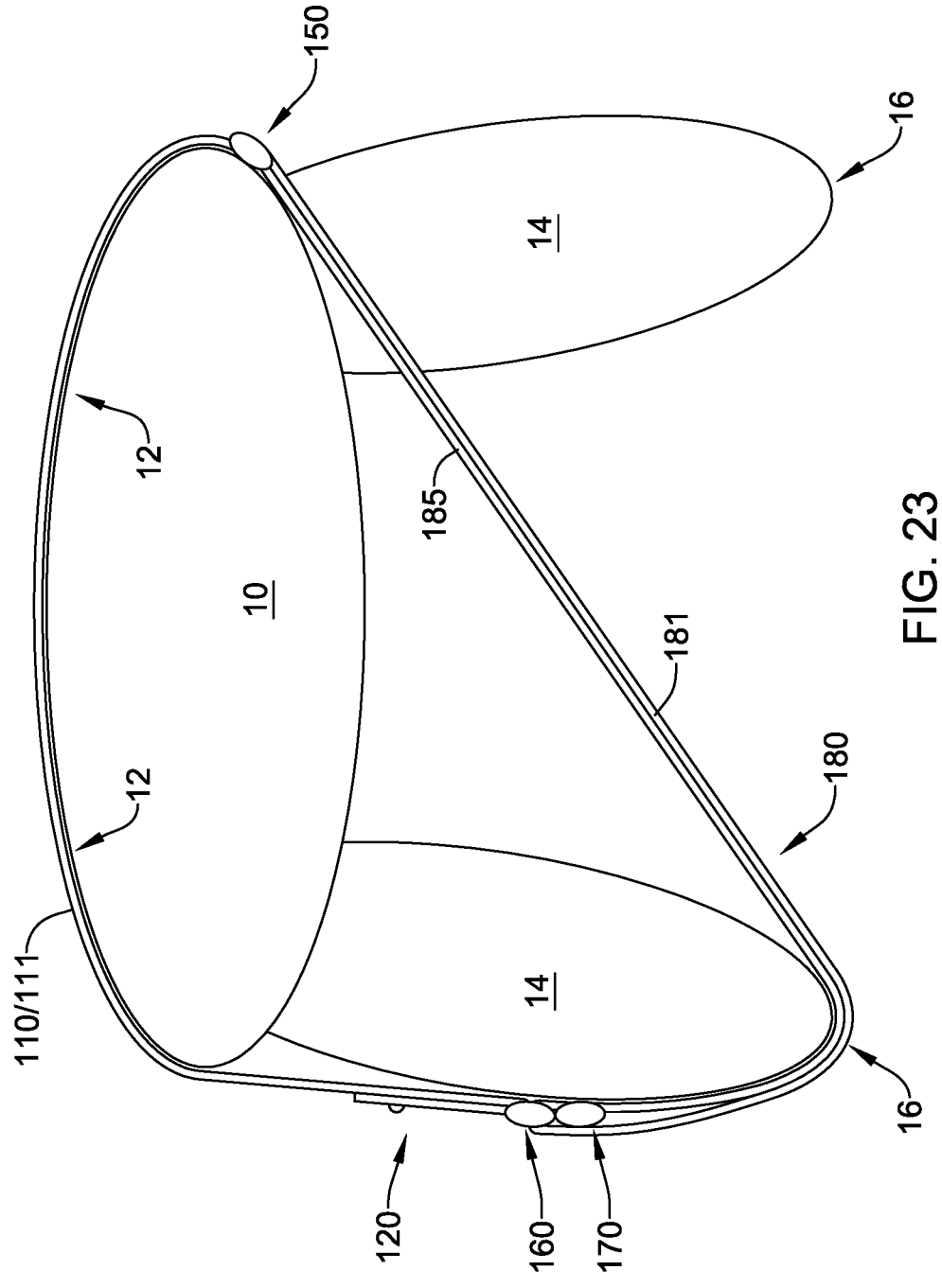
Figure 24:
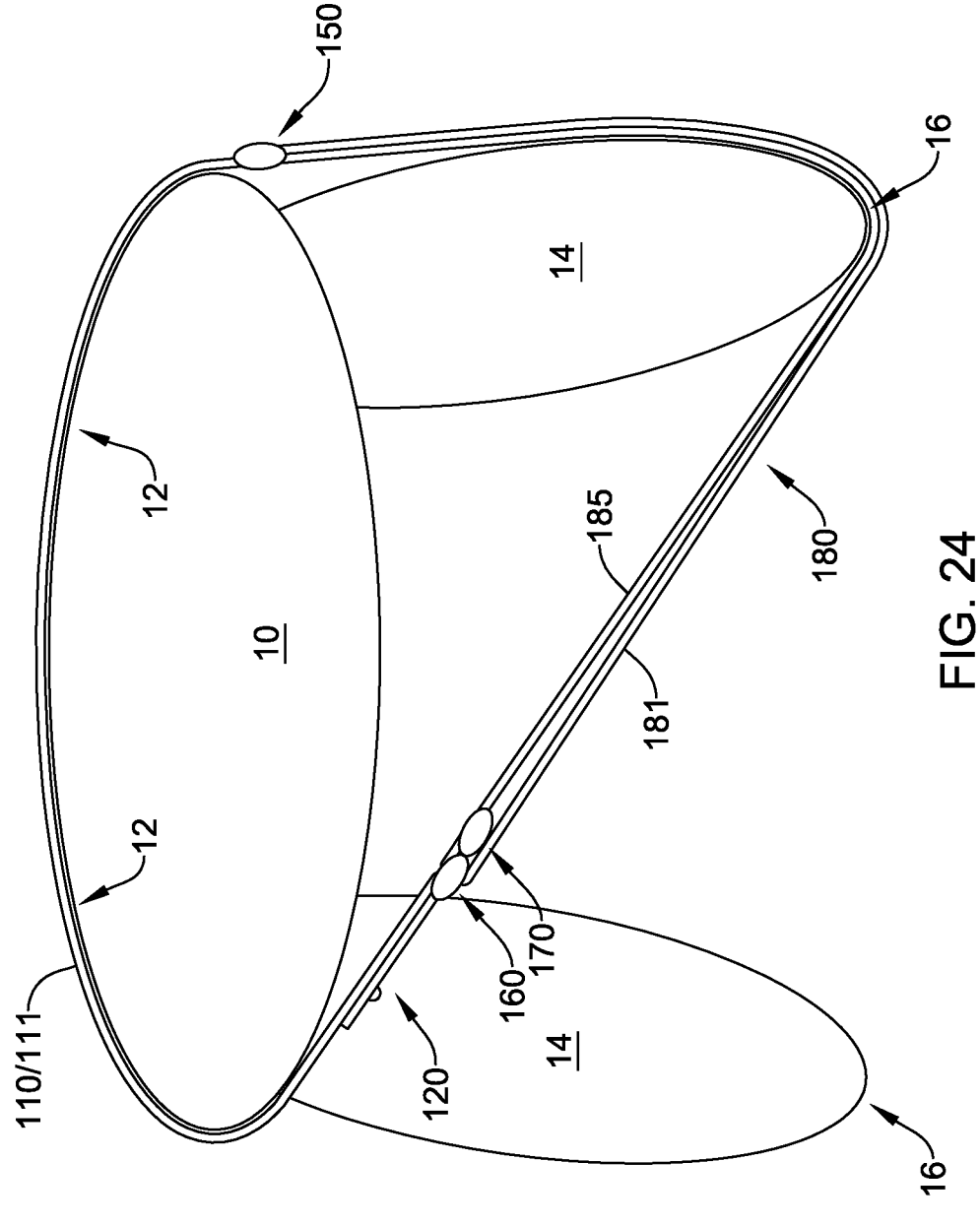

In some embodiments, the method may include moving the continuous loop from the first position to a second position in which the continuous loop extends around the lower back 12 of the user and at least one knee 16 of the user in the seated position such that the continuous loop exerts a radially inward force against the lower back 12 of the user in the second position, as seen in FIGS. 23-24, which schematically illustrates a top view of the user in the seated position with the continuous loop in the second position. The at least one knee 16 may be the user's right knee, as shown in FIG. 23, or the at least one knee 16 may be the user's left knee, as shown in FIG. 24. In some embodiments, position- ing the continuous loop around the left knee may be a preferred configuration and/or use of the back support device 100. In one non-limiting example, the continuous loop may be positioned around the lower back 12 of the user and the left knee of the user to use the back support device 100 while driving. Other configurations are also contem- plated. In some embodiments, the continuous loop may be moved from the right knee to the left knee, or from the left knee to the right knee, during use as desired for user comfort.

In some embodiments, in the second position, the con- tinuous loop may extend around the lower back 12 of the user and two knees of the user. In some embodiments, positioning the continuous loop around two knees may increase the radially inward force applied against the lower back 12 of the user compared to positioning the continuous loop around one knee. This may be useful if the user wants a temporary increase in the radially inward force (e.g., the amount of support) against the lower back 12 of the user without adjusting the first buckle position. In some embodi- ments, moving the continuous loop from the first position to the second position may elastically elongate the elastic strap 110 and/or the elongate piece of elastic material 111.

In some embodiments, the first clasping element 120 and the second buckle element 160 may be rotated off center on the torso 10 of the user when moving the continuous loop from the first position to the second position so that the first clasping element 120 and the second buckle element 160 are not positioned on and/or over the user's knee(s) in the second position. Some users may find having the first clasping element 120 and the second buckle element 160 positioning on and/or over the knee(s) uncomfortable. In some embodiments, in the second position, with the first clasping element 120 rotated toward the user's side (e.g., not centered on the torso 10), the continuous loop may extend around the lower back 12 of the user and the first segment 181 and the fifth segment 185 of the plurality of segments 180 may both extend around, over, and/or across the at least one knee 16, as seen in FIGS. 23-24 for example.

In some embodiments, the method may include sliding the first buckle element 150 along the medial portion 116 of the elastic strap 110 and/or the elongate piece of elastic material 111 to change the radially inward force against and/or applied to the lower back 12 of the user in the second position. The first buckle element 150 may be disposed in a first buckle position (marked with an "X" on the elastic strap 110 and/or the elongate piece of elastic material 111 in FIG. 25) when the radially inward force is at a desired level.

In some embodiments, the method may include moving the continuous loop from the second position to the first position without moving the first buckle element 150 from the first buckle position, wherein the elastic strap 110 and/or the elongate piece of elastic material 111 elastically con- tracts such that a perimeter length of the continuous loop in the first position is less than the perimeter length of the continuous loop in the second position.

Figure 26:
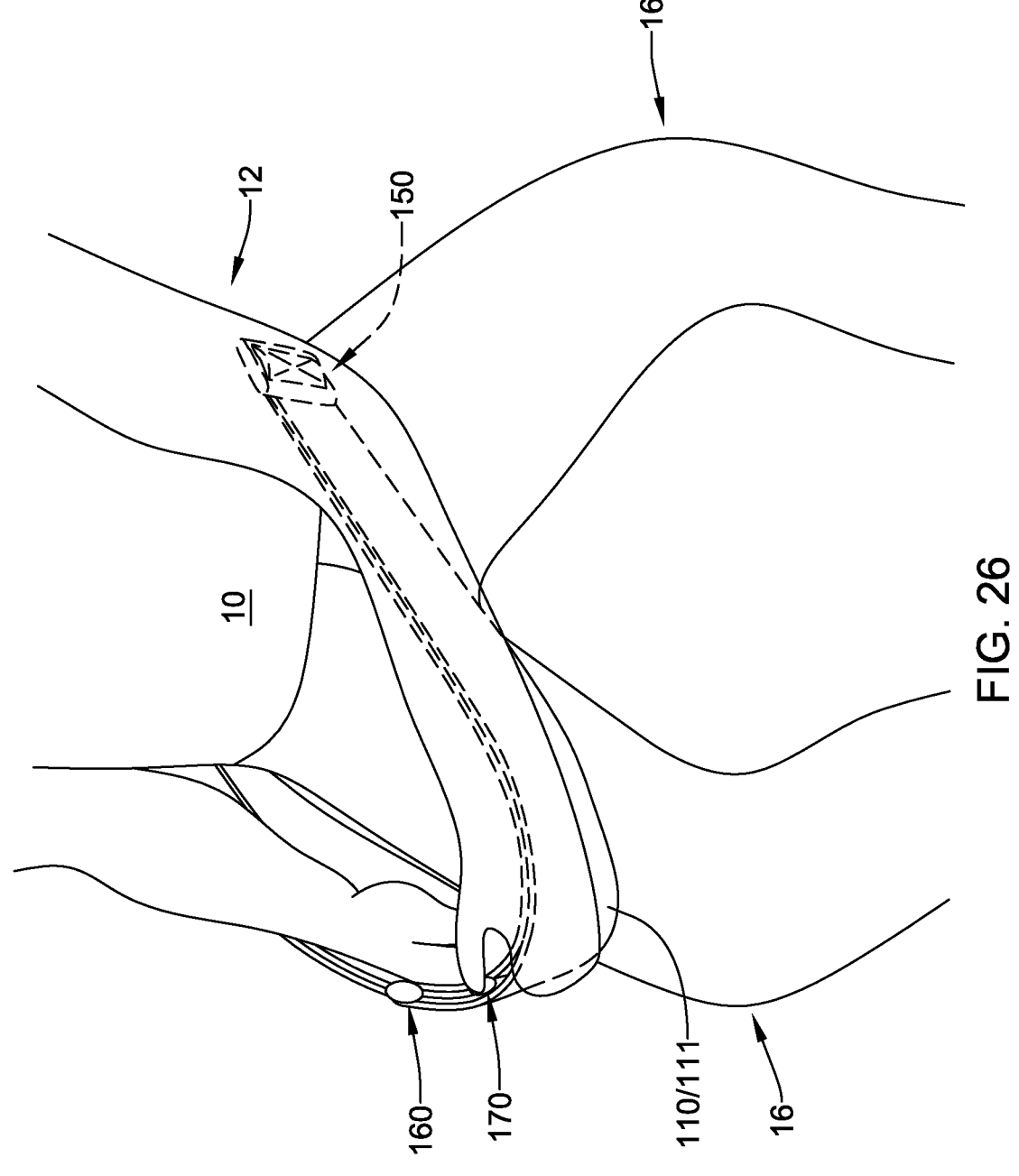
Figure 27:
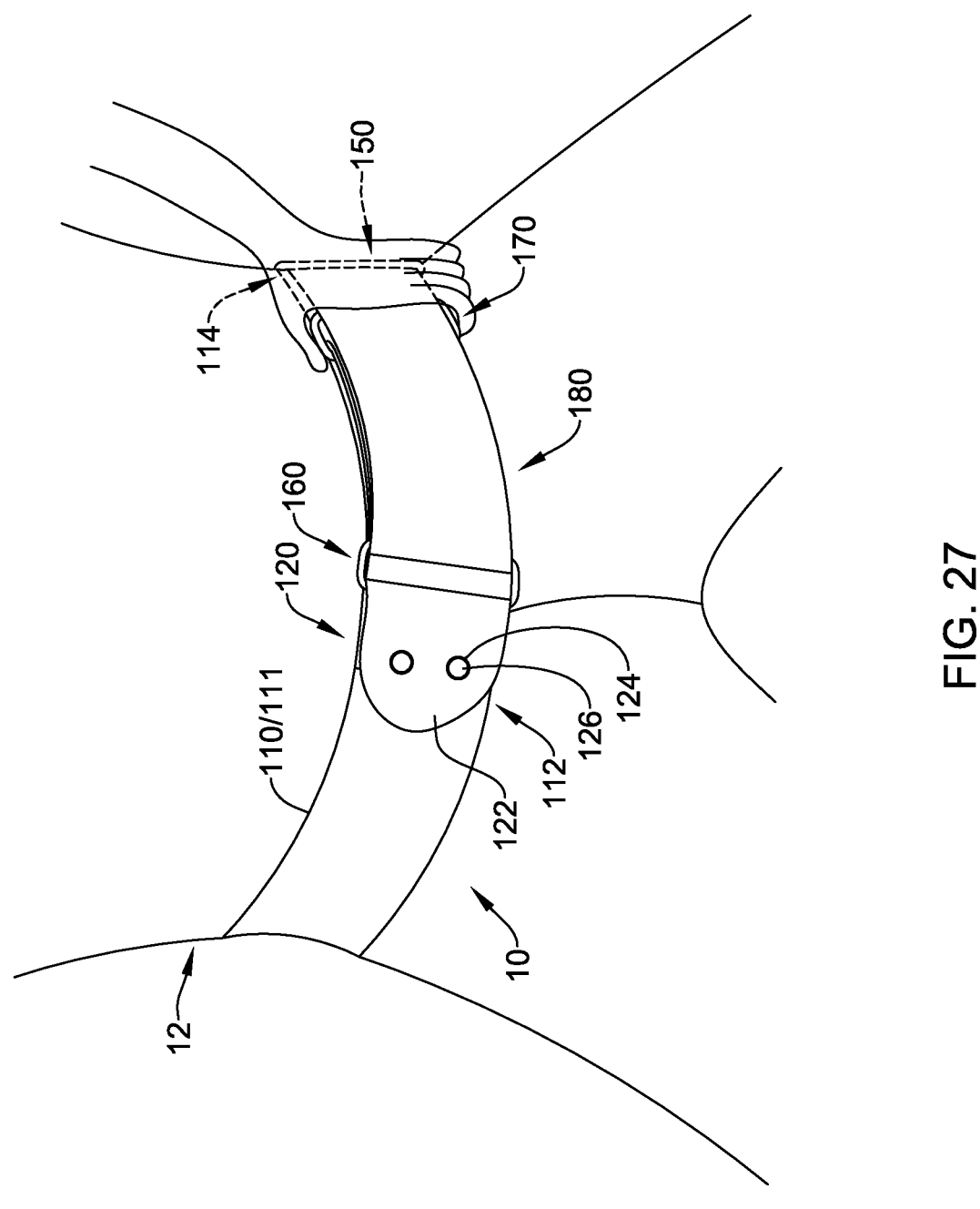

In some embodiments, moving the continuous loop from the second position to the first position may include sliding the third buckle element 170 over the medial portion 116 of the elastic strap 110 and/or the elongate piece of elastic material 111 to secure the continuous loop around the torso 10 of the user such that the continuous loop holds itself in place on the torso 10 of the user in the first position, as seen in FIGS. 26-27. As discussed herein, the third buckle ele- ment 170 may be disposed between the first buckle element 150 and the second buckle element 160.

In some embodiments, moving the continuous loop from the second position to the first position may include sliding the third buckle element 170 over the medial portion 116 of the elastic strap 110 and/or the elongate piece of elastic material 111 towards the first buckle element 150. In some embodiments, sliding the third buckle element 170 over the medial portion 116 of the elastic strap 110 and/or the elongate piece of elastic material 111 towards the first buckle element 150 forms the plurality of segments 180 of the elastic strap 110 and/or the elongate piece of elastic material 111 defined by the first buckle element 150, the second buckle element 160, and the third buckle element 170, as discussed herein. The plurality of segments 180 may circumferentially overlap between the first buckle element 150 and the second buckle element 160, as seen in FIG. 27.

In some embodiments, moving the continuous loop from the second position to the first position may cause slack to form and/or be disposed between the first buckle element 150 and the second buckle element 160. For example, when the user is tall, has long legs, and/or when the perimeter length of the continuous loop in the second position is sufficiently larger than the perimeter length of the continuous loop in the first position and/or when the first buckle element 150 is disposed in the first buckle position, elastic contraction of the elastic strap 110 and/or the elongate piece of elastic material 111 may be insufficient on its own to take up the difference between the perimeter length of the continuous loop in the second position and the perimeter length of the continuous loop in the first position. Accordingly, in some embodiments, sliding the third buckle element 170 over the medial portion 116 of the elastic strap 110 and/or the elongate piece of elastic material 111 may take up slack in the elastic strap 110 and/or the elongate piece of elastic material 111 disposed between the first buckle element 150 and the second buckle element 160 when the continuous loop is disposed in the first position. In some embodiments, sliding the third buckle element 170 over the medial portion 116 of the elastic strap 110 and/or the elongate piece of elastic material 111 may draw the second buckle element 160 closer to the first buckle element 150, as seen by comparing FIG. 26 to FIG. 27 for example.

Figure 25:
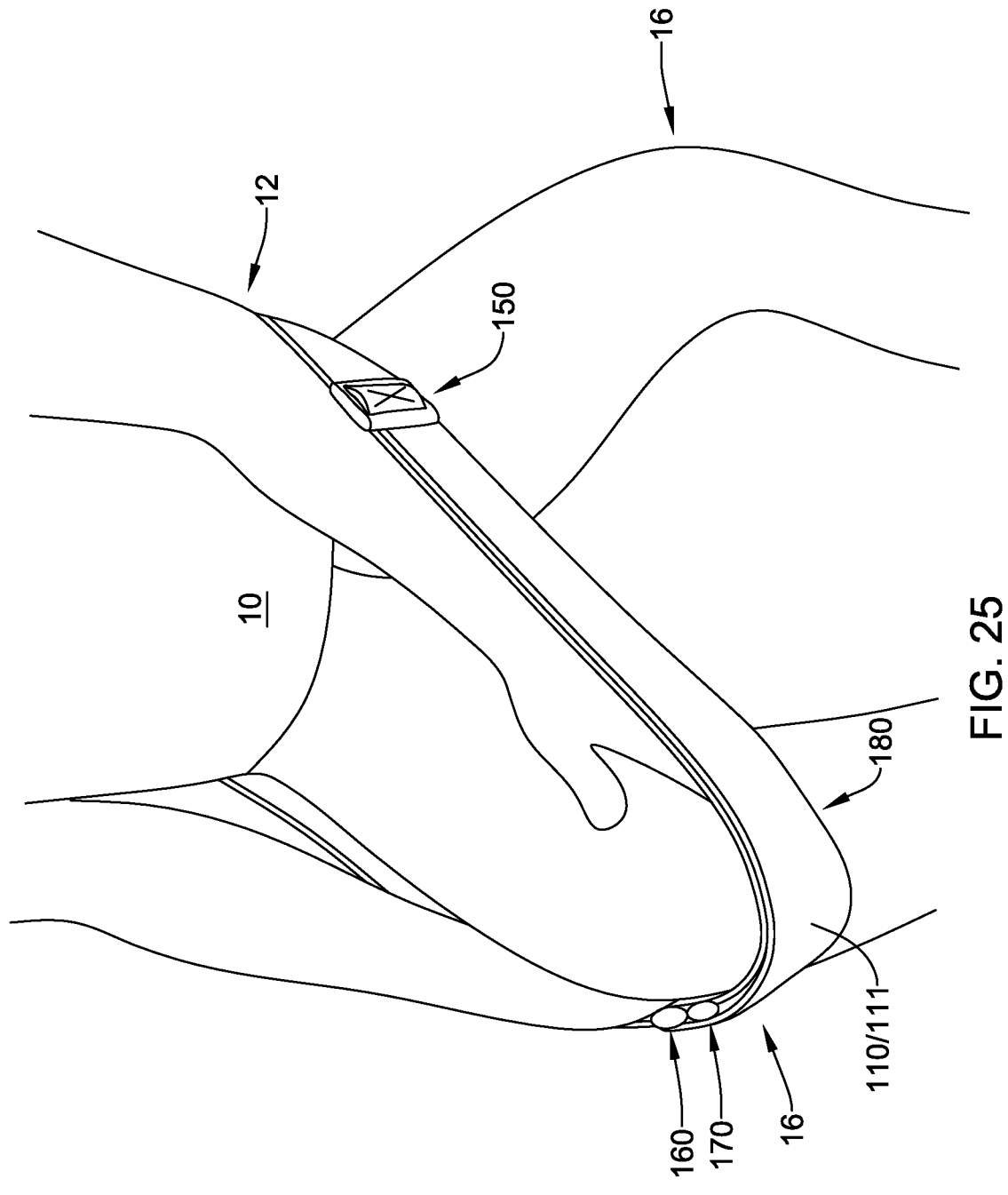

In some embodiments, the third buckle element 170 may be slidable over the medial portion 116 of the elastic strap 110 and/or the elongate piece of elastic material 111 between a retracted position when the continuous loop is disposed in the first position (e.g., FIGS. 21-22, 27-28) and an expanded position when the continuous loop is disposed in the second position (e.g., FIGS. 23-25). When the continuous loop is disposed in the first position and the third buckle element 170 is disposed in the retracted position, sufficient friction may exist between overlapping portions of the elastic strap 110 and/or the elongate piece of elastic material 111 within the third buckle element 170 to prevent the third buckle element 170 from sliding along the medial portion 116 of the elastic strap 110 and/or the elongate piece of elastic material 111. As the continuous loop is moved to the second position, elastic elongation of the elastic strap 110 and/or the elongate piece of elastic material 111 may exert force on the third buckle element 170 toward the second buckle element 160 sufficient to overcome the friction between overlapping portions of the elastic strap 110 and/or the elongate piece of elastic material 111 within the third buckle element 170, thereby causing the third buckle element 170 to slide along the medial portion 116 of the elastic strap 110 and/or the elongate piece of elastic material 111 toward the second buckle element 160.

After sliding the third buckle element 170 over the medial portion 116 of the elastic strap 110 and/or the elongate piece of elastic material 111 to take up slack in the elastic strap 110 and/or the elongate piece of elastic material 111 disposed between the first buckle element 150 and the second buckle element 160 when the continuous loop is disposed in the first position, and/or after sliding the third buckle element 170 to the retracted position, the elastic strap 110 and/or the elongate piece of elastic material 111 may be secured around the torso 10 of the user such that the continuous loop holds itself in place on the torso 10 of the user.

Once adjustments have been made to position the first buckle element 150 at the first buckle position and the radially inward force against and/or applied to the lower back 12 of the user in the second position is at the desired level, the back support device 100 and/or the continuous loop may be easily and repeatedly moved between the first position and the second position as described herein.

Generally, it is undesirable for the continuous loop to fall off of the torso 10 of the user if and/or when the user stands up. It is desirable for the continuous loop to remain in place on and/or around the torso 10 of the user in the first position for convenience and/or safety while being able to provide the desired level of radially inward force against the lower back 12 of the user in the second position. For example, if the user gets up to walk to another location, it is desirable for the continuous loop to remain in place on the torso 10 of the user instead of slipping down around the user's legs, which may cause a tripping hazard. Other benefits are also contemplated. As such, the continuous loop may be configured to fit snugly against the torso 10 of the user in the first position to maintain and/or hold itself in place on the torso 10 of the user.

Figure 28:
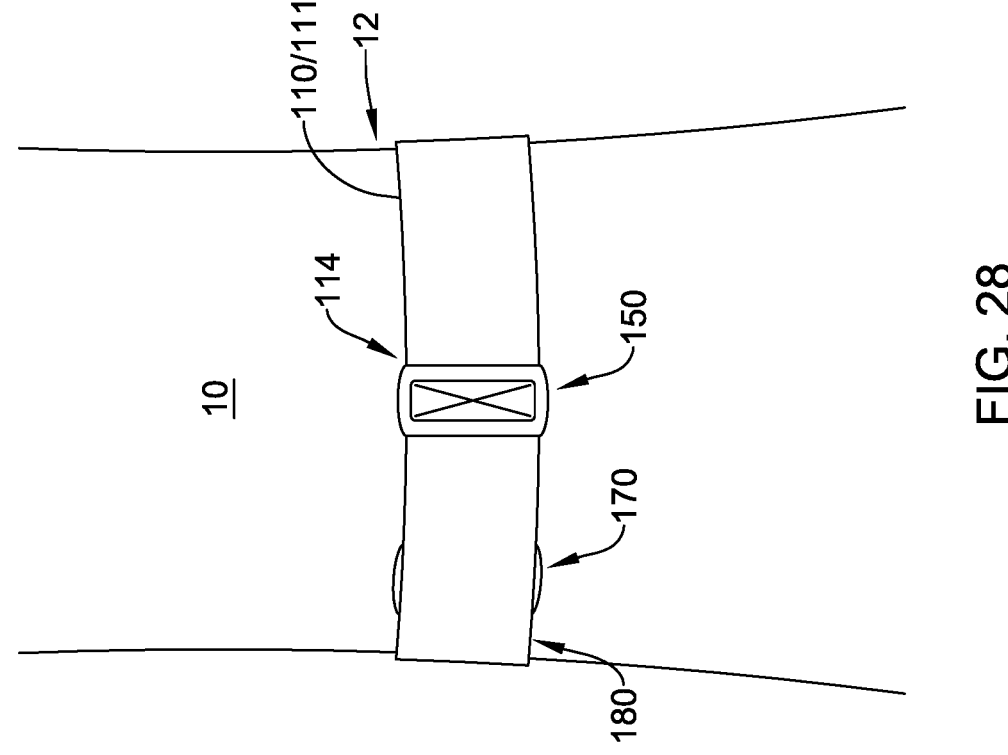

In some embodiments, the continuous loop may be movable between the first position in which the continuous loop is secured around the torso 10 of the user such that the continuous loop holds itself in place on the torso 10 of the user and the second position in which the continuous loop extends around the lower back 12 of the user and at least one knee 16 of the user. In some embodiments, the continuous loop may be movable between the first position and the second position via a combination of movement of the third buckle element 170 along the medial portion 116 of the elastic strap 110 and/or the elongate piece of elastic material 111 and elastic elongation of the elastic strap 110 and/or the elongate piece of elastic material 111. As discussed herein, the continuous loop may exert the radially inward force against the lower back 12 of the user in the second position to support the lower back 12 of the user. In at least some embodiments, in the second position, the first buckle element 150 may be disposed at the first buckle position and the continuous loop may be movable between the first position and the second position without moving the first buckle element 150 from the first buckle position (marked with an "X" on the elastic strap 110 and/or the elongate piece of elastic material 111, as seen in FIGS. 25, 26, and 28). For reference, FIG. 28 is a view of the arrangement shown in FIG. 27 from the left of the torso 10 of the user (e.g., from the right side of the view shown in FIG. 27) after the user's left hand has been removed from the third buckle element 170. In FIG. 28, the first buckle element 150 may be seen as having remained in the first position.

Figure 29:
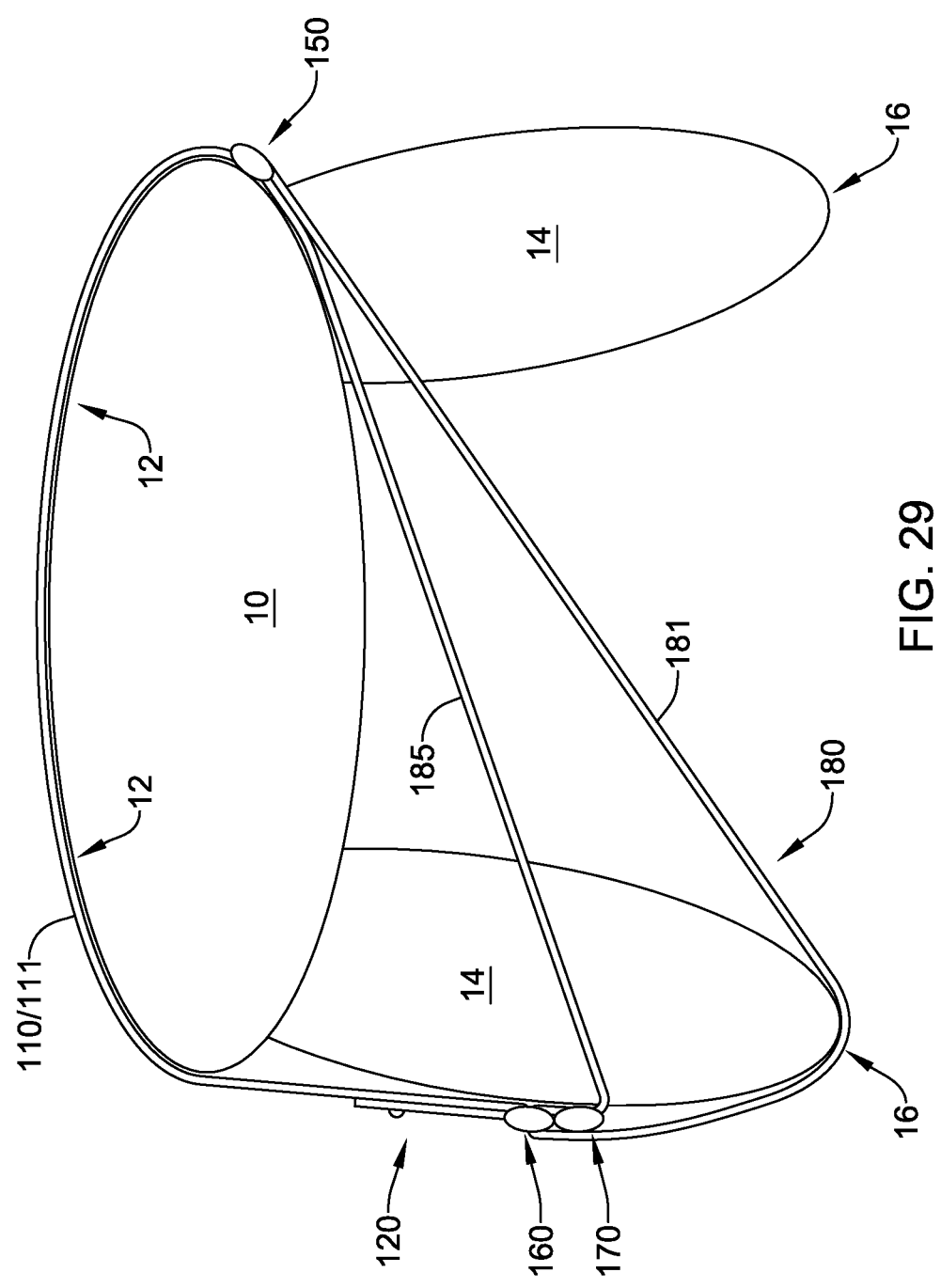
Figure 30:
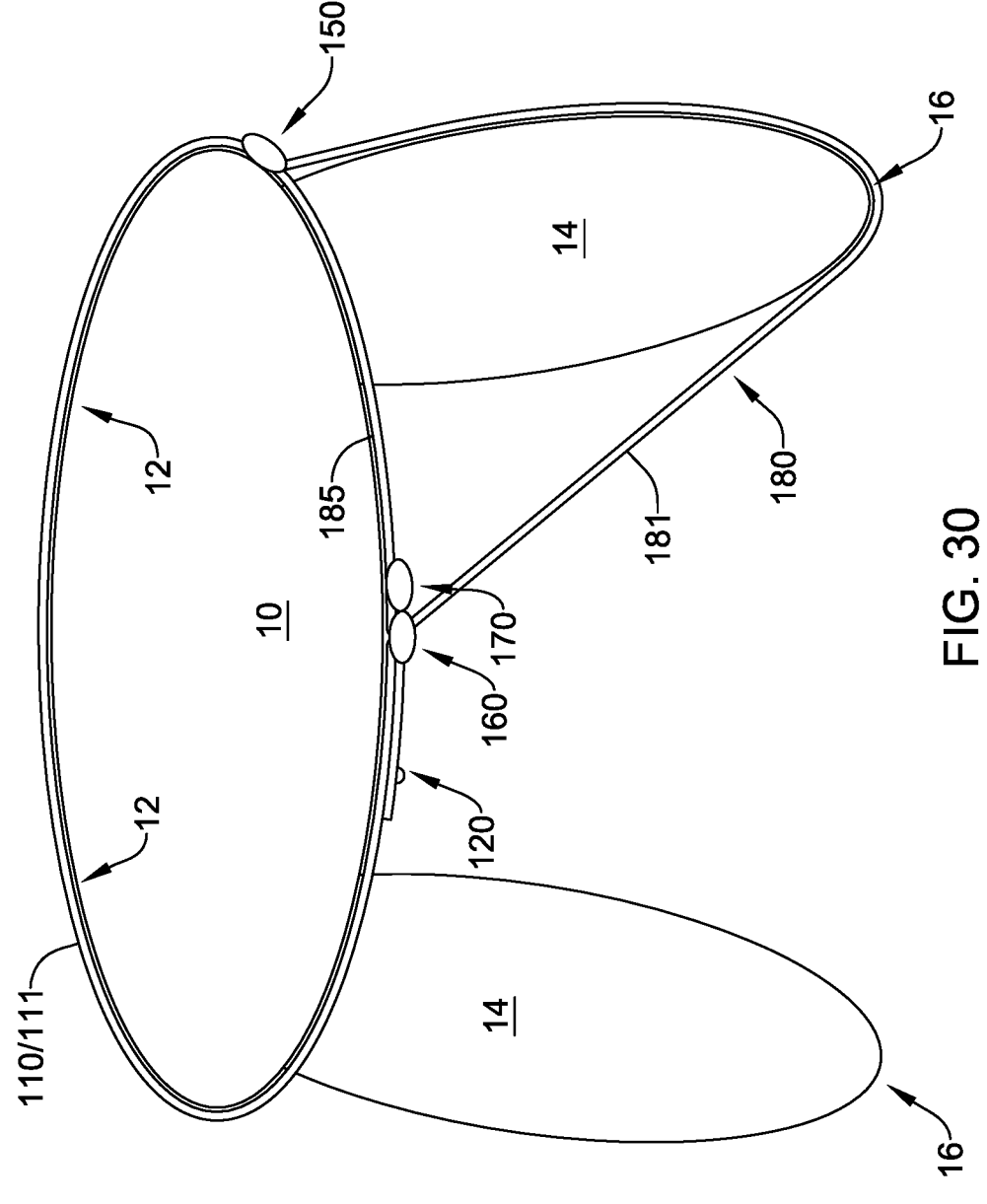

As discussed above, in some embodiments, the first clasping element 120 and the second buckle element 160 may be rotated off center on the torso 10 of the user when moving the continuous loop from the first position to the second position so that the first clasping element 120 and the second buckle element 160 are not positioned on and/or over the user's knee(s) in the second position. Some users may find having the first clasping element 120 and the second buckle element 160 positioning on and/or over the knee(s)

uncomfortable. Additionally, in some embodiments, the user may desire to have the radially inward force be less than the desired level set by the first buckle element 150 being disposed at the first buckle position. In some embodiments, with the first clasping element 120 rotated toward the user's side (e.g., not centered on the torso 10), the elastic strap 110 and/or the elongate piece of elastic material 111 may be movable from the first position in which the continuous loop is secured around the torso 10 of the user and a third position in which the first segment 181 of the plurality of segments 180 extends around at least one knee 16 of the user and the fifth segment of the plurality of segments 180 does not extend around at least one knee of the user, as seen in FIGS. 29-30. In some embodiments, the at least one knee 16 may be the right knee of the user, as shown in FIG. 29, and in some embodiments, the at least one knee 16 may be the left knee of the user, as shown in FIG. 30. In some embodiments, the first segment 181 of the plurality of segments 180 may be moved between the left knee and the right knee during use.

This arrangement (e.g., a single segment of the elastic strap 110 and/or the elongate piece of elastic material 111 extending around at least one knee 16) reduces the radially inward force applied to the lower back 12 of the user. For example, in some embodiments, the elastic strap 110 and/or the elongate piece of elastic material 111 is not being elongated to the same degree as when both the first segment 181 and the fifth segment 185 of the plurality of segments 180 extend around the at least one knee 16. Similar to above, the elastic strap 110 and/or the elongate piece of elastic material 111 may be moved between the first position and the third position without moving the first buckle element 150 from the first buckle position. In some alternative embodiments, the first segment 181 may extend around two knees while the fifth segment does not extend around any knees of the user.

In some embodiments, positioning the first segment 181 around the left knee of the user with the first clasping element 120 positioned generally between the legs 14 of the user along the torso 10 of the user, the fifth segment 185 may draw compressively against the user's stomach to create a girdling effect while the first segment 181 and the left knee provide support to the lower back 12 of the user. In some embodiments, positioning the first segment 181 around the left knee of the user may be a preferred configuration and/or use of the back support device 100. In one non-limiting example, the elastic strap 110 may be positioned around the lower back 12 of the user and the first segment 181 around the left knee of the user to use the back support device 100 while driving. Other configurations are also contemplated.

Figure 31:
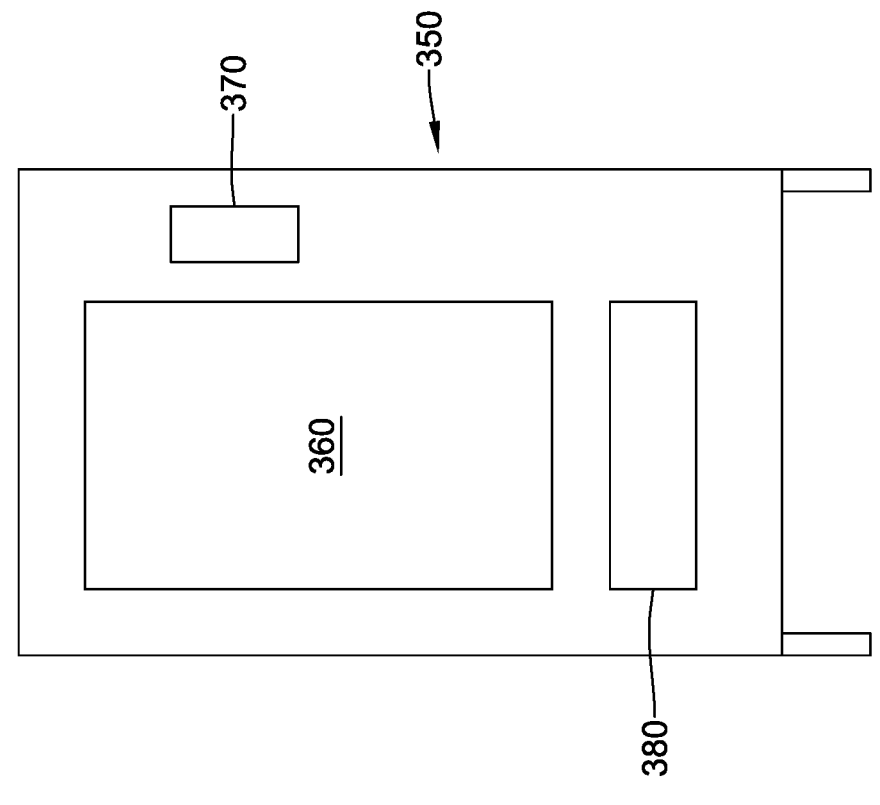
FIG. 31 illustrates selected aspects of a kiosk for marketing the back support device(s).
Figure 31:
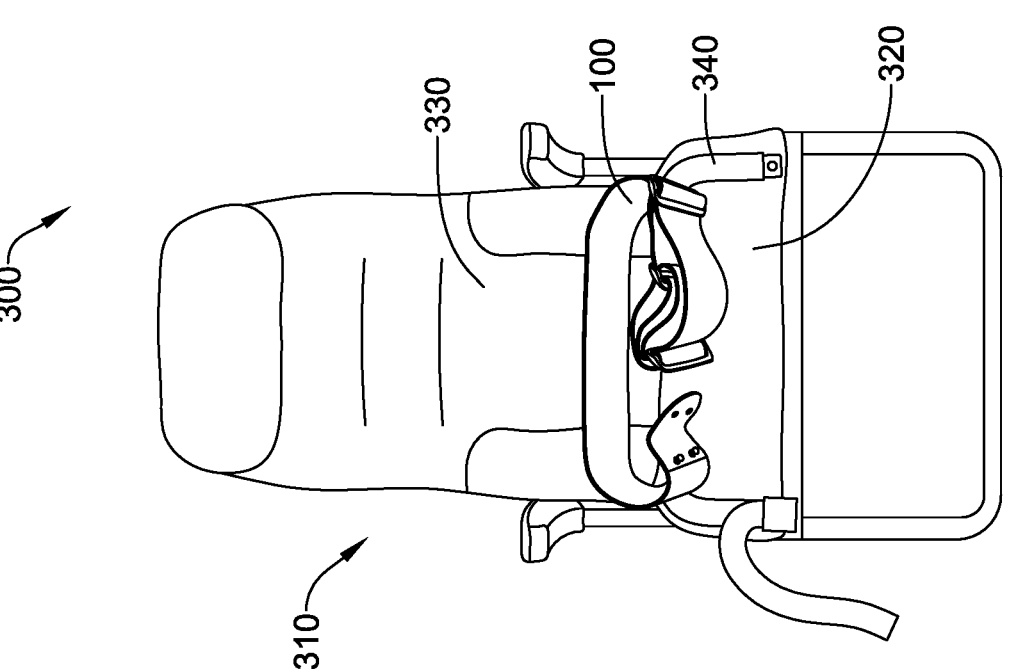

FIG. 31 illustrates selected aspects of a kiosk 300 for marketing the back support device 100 for supporting a lower back of a user. The kiosk 300 may include a seat 310 including a seating surface 320 and a backrest 330. In some embodiments, the seat 310 may be a seat type with which it may be desirable to use the back support device 100, such as but not limited to a stadium seat, an airport concourse seat, an airline seat, an automobile seat, a bench, etc.

The kiosk 300 may include the back support device 100 secured to the backrest 330. In at least some embodiments, the back support device 100 may be secured to the backrest 330 in a theft resistant manner. In some embodiments, the back support device 100 may be fixedly secured to the backrest 330, such as with stitching, adhesive, or other permanent attachment means. In some embodiments, the back support device 100 may be removably secured to the backrest 330 to facilitate cleaning and/or replacement. In some embodiments, a sleeve may be fixedly attached to the backrest 330. The sleeve may be configured to receive the back support device 100 therein and/or therethrough. In at least some embodiments, the sleeve and/or the back support device 100 may be configured to prevent removal of the back support device 100 from the sleeve except through proprietary means which may serve to reduce and/or prevent theft. Other configurations are also contemplated.

In some embodiments, the seat 310 may optionally include a safety belt 340 (e.g., a seat belt, such as those associated with airline or automobile seats) secured thereto. In some embodiments, the safety belt 340 may be provided so that the user may assess the interaction of the safety belt 340 and the back support device 100 in use.

The kiosk 300 may include a vending machine 350 configured to hold stock 360 of the back support device 100 therein. In some embodiments, the stock 360 may include different versions and/or configurations of the back support device 100. In some embodiments, the stock 360 may include individually packaged back support devices. The vending machine 350 may include a payment mechanism 370 configured to facilitate sale of the stock 360. In some embodiments, the payment mechanism 370 may include one or more means of facilitating payment including but not limited to cash transactions and/or paperless transactions (e.g., credit card, debit card, electronic, touchless, etc.). The vending machine 350 may include a dispenser 380 configured to dispense and/or release the stock 360 to the user upon successful completion of a sale or transaction.

In some embodiments, the kiosk 300 may include multiple instances of the seat 310 and/or may include different versions and/or configurations of the back support device 100. For example, a first seat may include a first version and/or configuration of the back support device 100 secured thereto and a second seat may include a second version and/or configuration of the back support device 100 secured thereto. In some further embodiments, a third seat may include a third version and/or configuration of the back support device 100 secured thereto.

In some alternative embodiments, the seat 310 may be devoid of the backrest 330. In such embodiments, the back support device 100 may be secured to the seat 310 in a theft resistant manner. It shall be appreciated that a backrest is not required to receive the benefits of using the back support device 100 disclosed herein.

The materials that can be used for the various components of the back support device and the various elements thereof disclosed herein may include those commonly associated with belts, straps, etc. For simplicity purposes, the following discussion refers to the device. However, this is not intended to limit the devices and methods described herein, as the discussion may be applied to other elements and/or components disclosed herein, such as, but not limited to, the elastic strap, the first clasping element, the second clasping element, the clasping mechanism, the buckle element(s), etc. and/or elements or components thereof.

In some embodiments, the device and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM; for example, DELRIN®), polyether block ester, polyurethane, polypropylene (PP), polyvinylchloride (PVC), polyether-ester, ether or ester based copolymers (for example, butylene/poly(alkylene ether) phthalate and/or other polyester elastomers), polyamide, elastomeric poly-amides, block polyamide/ethers, polyether block amide (PEBA; for example, PEBAX®), ethylene vinyl acetate copolymers (EVA), silicones, polyethylene (PE), high-den-sity polyethylene (HDPE), low-density polyethylene, linear low density polyethylene, polyester, polybutylene tereph-thalate (PBT), polyethylene terephthalate (PET), polytrim-ethylene terephthalate, polyethylene naphthalate (PEN), polyetheretherketone (PEEK), polyimide (PI), polyetherim-ide (PEI), polyphenylene sulfide (PPS), polyphenylene oxide (PPO), poly paraphenylene terephthalamide (for example, KEVLAR®), polysulfone, nylon, nylon-12, per-fluoro(propyl vinyl ether) (PFA), ethylene vinyl alcohol, polyolefin, polystyrene, epoxy, polyvinylidene chloride (PVdC), poly(styrene-b-isobutylene-b-styrene), polycarbon-ates, polyurethane silicone copolymers, biocompatible poly-mers, other suitable materials, or mixtures, combinations, copolymers thereof, and the like.

Some examples of suitable metals and metal alloys include aluminum; aluminum alloys; stainless steel; mild steel; nickel alloys; combinations thereof; or any other suitable material.

In some embodiments, the device and/or components thereof may include a fabric material disposed over or within the structure. Some examples of suitable fabric materials include, but are not limited to, cotton, nylon, silk, polypropylene, polyester, spandex, elastane (e.g., LYCRA®), and the like, and/or blends or combinations thereof.

In some embodiments, the device and/or components thereof may include natural materials such as leather, silk, wood, hemp, plant matter, animal hide, stone, etc. and/or combinations thereof. In some embodiments, the natural materials may be used alone or in combination with other materials.

In some embodiments, the device and/or components thereof may include and/or be formed from a textile mate-rial. Some examples of suitable textile materials may include synthetic yarns that may be flat, shaped, twisted, textured, pre-shrunk or un-shrunk. Synthetic yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, natural silk, and polytetrafluoroethylenes. Moreover, at least one of the synthetic yarns may be a metallic yarn or a glass or ceramic yarn or fiber. In some embodiments, the yarns may further include carbon, glass, or ceramic fibers. The yarns may be of the multifilament, monofilament, or spun types. The type and denier of the yarn chosen may be selected in a manner which has desirable properties for the intended use.

It should be understood that this disclosure is, in many respects, only illustrative. Changes may be made to details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A back support device for supporting a lower back of a user, comprising:
   an elastic strap;

a first clasping element attached to a first end of the elastic strap;
   a second clasping element slidably disposed over the elastic strap and configured to releasably engage the first clasping element to form a continuous loop; and
   a buckle element secured to a second end of the elastic strap;
   wherein the buckle element is slidably disposed on a medial portion of the elastic strap for adjusting a perimeter length of the continuous loop;
   wherein the continuous loop is movable between a first position in which the continuous loop has a first perim-eter length and a second position in which the continu-ous loop has a second perimeter length via elastic elongation;
   wherein the first perimeter length is less than the second perimeter length.

2. The back support device of claim 1, wherein the second clasping element includes a closed loop.

3. The back support device of claim 2, wherein the first clasping element is configured to extend through the closed loop of the second clasping element and fold back on itself to form the continuous loop.

4. The back support device of claim 3, wherein the first clasping element is configured to releasably secure to itself.

5. The back support device of claim 1, wherein in the first position the continuous loop is secured around a torso of the user such that the continuous loop holds itself in place on the torso of the user and in the second position the continuous loop extends around the lower back of the user and at least one knee of the user in a seated position.

6. The back support device of claim 5, wherein in the second position the continuous loop extends around the lower back of the user and two knees of the user.

7. The back support device of claim 1, wherein the first clasping element includes a non-elastic flap.

8. The back support device of claim 1, wherein the medial portion of the elastic strap extends through the buckle element.

9. A back support device for supporting a lower back of a user, comprising:
   an elastic strap;
   a first clasping element attached to a first end of the elastic strap;
   a first buckle element secured to a second end of the elastic strap and slidably disposed over a medial por-tion of the elastic strap;
   a second buckle element slidably disposed over the elastic strap and configured to releasably engage the first clasping element to form a continuous loop; and
   a third buckle element slidably disposed over the elastic strap between the first buckle element and the second buckle element;
   wherein a plurality of segments of the elastic strap is defined by the first buckle element, the second buckle element, and the third buckle element, and the plurality of segments circumferentially overlap between the first buckle element and the second buckle element.

10. The back support device of claim 9, wherein the continuous loop is movable between a first position in which the continuous loop is secured around a torso of the user such that the continuous loop stays in place on the torso of the user and a second position when the continuous loop extends around the lower back of the user and at least one knee of the user.

11. The back support device of claim 10, wherein the continuous loop is movable between the first position and the second position via a combination of movement of the third buckle element and elastic elongation of the elastic strap.

12. The back support device of claim 10, wherein the continuous loop exerts a radially inward force against the lower back of the user when in the second position to support the lower back of the user.

13. The back support device of claim 10, wherein in the second position, the first buckle element is disposed at a first buckle position, and the continuous loop is movable between the first position and the second position without moving the first buckle element from the first buckle position.

14. The back support device of claim 9, wherein the plurality of segments includes a first segment extending between the first buckle element and the second buckle element, a second segment extending between the second buckle element and the third buckle element, a third segment extending between the third buckle element and the second buckle element, a fourth segment extending between the second buckle element and the third buckle element, and a fifth segment extending between the third buckle element and the first buckle element.

15. The back support device of claim 14, wherein the first segment is disposed radially outward of all other segments of the plurality of segments.

16. The back support device of claim 14, wherein the second segment is disposed radially inward of the first segment, the third segment is disposed radially inward of the second segment, and the fourth segment is disposed radially inward of the third segment.

17. A method of supporting a lower back of a user, comprising:

positioning an elastic strap around a torso of the user, the elastic strap including a first end and a second end, the second end being secured to a first buckle element slidably disposed on a medial portion of the elastic strap;

releasably securing a first clasping element attached to the first end of the elastic strap to a second buckle element slidably disposed over the elastic strap to form a continuous loop around the torso of the user in a first position;

moving the continuous loop from the first position to a second position in which the continuous loop extends around the lower back of the user and at least one knee of the user in a seated position such that the continuous loop exerts a radially inward force against the lower back of the user;

sliding the first buckle element along the medial portion of the elastic strap to change the radially inward force applied to the lower back of the user in the second position, the first buckle element being disposed in a first buckle position when the radially inward force is at a desired level; and moving the continuous loop from the second position to the first position without moving the first buckle element from the first buckle position, wherein the elastic strap elastically contracts such that a perimeter length of the continuous loop in the first position that is less than the perimeter length of the continuous loop in the second position.

18. The method of claim 17, wherein moving the continuous loop from the second position to the first position includes sliding a third buckle element over the medial portion of the elastic strap to secure the continuous loop around the torso of the user such that the continuous loop stays in place on the torso of the user in the first position.

19. The method of claim 18, wherein the third buckle element is disposed between the first buckle element and the second buckle element.

20. The method of claim 19, wherein moving the continuous loop from the second position to the first position includes sliding the third buckle element over the medial portion of the elastic strap towards the first buckle element.

21. The method of claim 20, wherein sliding the third buckle element over the medial portion of the elastic strap towards the first buckle element forms a plurality of segments of the elastic strap defined by the first buckle element, the second buckle element, and the third buckle element;

wherein the plurality of segments circumferentially overlap between the first buckle element and the second buckle element.

22. The method of claim 18, wherein sliding the third buckle element over the medial portion of the elastic strap takes up slack in the elastic strap disposed between the first buckle element and the second buckle element when the continuous loop is disposed in the first position.

23. The method of claim 18, wherein sliding the third buckle element over the medial portion of the elastic strap draws the second buckle element closer to the first buckle element.

24. The method of claim 17, wherein moving the continuous loop from the first position to the second position elastically elongates the elastic strap.

25. A method of supporting a lower back of a user, comprising:

positioning an elastic strap around a torso of the user, the elastic strap including a first end and a second end, the second end being secured to a buckle element slidably disposed on a medial portion of the elastic strap;

releasably securing a first clasping element attached to the first end of the elastic strap to a second clasping element slidably disposed over the elastic strap to form a continuous loop around the torso of the user;

sliding the buckle element along the medial portion of the elastic strap to secure the continuous loop around the torso of the user such that the continuous loop holds itself in place on the torso of the user in a first position, wherein the continuous loop has a first perimeter length in the first position; and moving the continuous loop from the first position to a second position in which the continuous loop extends around the lower back of the user and at least one knee of the user in a seated position, wherein the elastic strap elastically elongates from the first position to the second position such that in the second position the continuous loop has a second perimeter length greater than the first perimeter length.

26. The method of claim 25, wherein the buckle element includes a first end member, a second end member, a first side member extending from the first end member to the second end member, a second side member extending from the first end member to the second end member, and a central member disposed between the first side member and the second side member, the central member extending from the first end member to the second end member.

27. The method of claim 26, wherein the second end of the elastic strap is fixedly secured to the central member and the medial portion of the elastic strap extends between the first side member and the central member and the medial portion of the elastic strap extends between the second side member and the central member.

28. The method of claim 25, further comprising moving the continuous loop from the second position to the first position without any adjustment other than elastic contraction.

29. The method of claim 25, wherein the continuous loop radially constricts upon the torso of the user in the first position.

30. The method of claim 25, further comprising sliding the buckle element along the medial portion of the elastic strap in the first position to change a radially inward force exerted by the continuous loop against the lower back of the user in the second position.

31. A back support device for supporting a lower back of a user, comprising:

an elongate piece of elastic material;

a first clasping element attached to a first end of the elongate piece of elastic material;

a buckle element secured to a second end of the elongate piece of elastic material; and a second clasping element slidably disposed over the elongate piece of elastic material and configured to releasably engage the first clasping element;

wherein a medial portion of the elongate piece of elastic material passes through the buckle element such that the buckle element is disposed at a buckle position along the medial portion;

wherein the second clasping element is slidably disposed over the elongate piece of elastic material between the second end of the elongate piece of elastic material and the buckle position;

wherein the back support device is movable, without changing the buckle position, between a first position in which the back support device forms a continuous loop extending around and elastically constricting upon a torso of the user and a second position in which the continuous loop extends around the lower back of the user and at least one knee of the user in a seated position.

32. The back support device of claim 31, wherein the continuous loop has a first perimeter length in the first position and a second perimeter length in the second position, the second perimeter length being greater than the first perimeter length.

33. The back support device of claim 32, wherein the back support device is movable between the first position and the second position only via elasticity of the elongate piece of elastic material.

34. The back support device of claim 31, wherein the first clasping element includes an aperture extending therethrough and a projecting element fixedly attached thereto, wherein the projecting element is configured to extend through the aperture to secure the first clasping element to itself when the first clasping element is engaged with the second clasping element to form the continuous loop.

35. The back support device of claim 34, wherein the first clasping element comprises leather and the projecting element is a metal stud.

36. The back support device of claim 31, wherein the elongate piece of elastic material includes a first layer and a second layer, wherein at least a portion of the first clasping element extends between the first layer and the second layer of the elongate piece of elastic material.

* * * * *